US010568527B2

(12) United States Patent
Yoon et al.

(10) Patent No.: US 10,568,527 B2
(45) Date of Patent: Feb. 25, 2020

(54) APPARATUS FOR AND METHOD OF MONITORING BLOOD PRESSURE AND WEARABLE DEVICE HAVING FUNCTION OF MONITORING BLOOD PRESSURE

(71) Applicant: SAMSUNG ELECTRONICS CO., LTD., Suwon-si (KR)

(72) Inventors: Youngzoon Yoon, Hwaseong-si (KR); Jaesoong Lee, Suwon-si (KR); Jisoo Kyoung, Seoul (KR); Younggeun Roh, Seoul (KR); Yeonsang Park, Seoul (KR); Chanwook Baik, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 74 days.

(21) Appl. No.: 14/844,437

(22) Filed: Sep. 3, 2015

(65) Prior Publication Data
US 2016/0058300 A1 Mar. 3, 2016

(30) Foreign Application Priority Data

Sep. 3, 2014 (KR) .................. 10-2014-0117254

(51) Int. Cl.
*A61B 5/021* (2006.01)
*A61B 5/0295* (2006.01)
(Continued)

(52) U.S. Cl.
CPC ............ *A61B 5/021* (2013.01); *A61B 5/0059* (2013.01); *A61B 5/0295* (2013.01); *A61B 5/681* (2013.01);
(Continued)

(58) Field of Classification Search
CPC ..... A61B 5/021; A61B 5/0295; A61B 5/0059; A61B 5/0002; A61B 5/0261;
(Continued)

(56) References Cited

U.S. PATENT DOCUMENTS 4,987,900 A 1/1991 Eckerle et al.
5,065,765 A 11/1991 Eckerle et al.
(Continued)

FOREIGN PATENT DOCUMENTS

CN 104257371 A 1/2015
CN 104970781 A 10/2015
(Continued)

OTHER PUBLICATIONS

Zhang et al; "A LabVIEW Based Measure System for Pulse Wave Transit Time"; Proceedings of the 5th International Conference on Information Technology and Application in Biomedicine, in conjunction with the 2nd International Symposium & Summer School on Biomedical and Health Engineering; May 30-31, 2008; 4 pgs. Total, pp. 477-480.
(Continued)

*Primary Examiner* — Angela M Hoffa
(74) *Attorney, Agent, or Firm* — Sughrue Mion, PLLC

(57) ABSTRACT

A method of monitoring a blood pressure includes: emitting a laser to a blood vessel in a body part; detecting, from the body part, laser speckles caused by scattering of the emitted laser; obtaining a bio-signal indicating a change in a volume of the blood vessel by using the detected laser speckles; and estimating a blood pressure based on the obtained bio-signal.

17 Claims, 27 Drawing Sheets

- LD: Laser Diode
- PD: Photo Diode

(51) Int. Cl.
*A61B 5/00* (2006.01)
*A61B 5/026* (2006.01)
*A61B 5/024* (2006.01)

(52) U.S. Cl.
CPC ........... *A61B 5/0002* (2013.01); *A61B 5/0261* (2013.01); *A61B 5/02416* (2013.01); *A61B 5/02438* (2013.01); *A61B 5/6803* (2013.01); *A61B 5/7235* (2013.01); *A61B 2562/0233* (2013.01); *A61B 2562/046* (2013.01); *A61B 2562/12* (2013.01)

(58) Field of Classification Search
CPC ...... A61B 2562/046; A61B 2562/0233; A61B 5/6803; A61B 5/02438; A61B 5/02416; A61B 2562/12; A61B 5/7235; A61B 5/02116; A61B 5/02125; A61B 5/02141; A61B 5/02427; A61B 5/02433; A61B 5/02444
See application file for complete search history.

(56) References Cited

U.S. PATENT DOCUMENTS

| | | | |
|---|---|---|---|
| 5,265,011 A | 11/1993 | O'Rourke | |
| 5,891,022 A | 4/1999 | Pologe | |
| 6,095,984 A | 8/2000 | Amano et al. | |
| 6,161,038 A | 12/2000 | Schookin et al. | |
| 6,475,153 B1 | 11/2002 | Khair et al. | |
| 6,571,193 B1 | 5/2003 | Unuma et al. | |
| 7,123,363 B2 | 10/2006 | Puttappa et al. | |
| 7,231,243 B2* | 6/2007 | Tearney | A61B 1/00082 600/407 |
| 7,463,796 B2* | 12/2008 | Borgos | A61B 5/022 250/227.11 |
| 7,641,614 B2 | 1/2010 | Asada et al. | |
| 7,657,135 B2* | 2/2010 | Borgos | A61B 5/022 250/227.11 |
| 7,737,947 B2* | 6/2010 | Schroeder | G06F 3/0317 345/166 |
| 7,822,299 B2* | 10/2010 | Borgos | A61B 5/022 385/1 |
| 7,925,056 B2* | 4/2011 | Presura | G06K 9/0012 356/28 |
| 8,032,200 B2* | 10/2011 | Tearney | A61B 1/00082 600/407 |
| 8,089,465 B2* | 1/2012 | Lutian | G06F 3/0317 250/221 |
| 8,111,953 B2* | 2/2012 | Borgos | A61B 5/022 385/1 |
| 8,217,897 B2* | 7/2012 | Lutian | G06F 3/0317 250/221 |
| 8,277,384 B2* | 10/2012 | Fine | A61B 5/14551 600/481 |
| 8,313,439 B2 | 11/2012 | McCombie et al. | |
| 8,343,062 B2 | 1/2013 | Fortin et al. | |
| 8,343,063 B2* | 1/2013 | Borgos | A61B 5/02225 600/490 |
| 8,360,985 B2* | 1/2013 | Borgos | A61B 5/02225 600/500 |
| 8,467,636 B2* | 6/2013 | Borgos | A61B 5/022 385/1 |
| 8,496,595 B2 | 7/2013 | Jornod | |
| 8,808,188 B2 | 8/2014 | Banet et al. | |
| 8,868,149 B2* | 10/2014 | Eisen | A61B 5/14552 600/324 |
| 8,954,135 B2* | 2/2015 | Yuen | H04W 4/027 600/476 |
| 9,097,516 B2 | 8/2015 | Hotta et al. | |
| 9,149,216 B2* | 10/2015 | Eisen | A61B 5/14552 |
| 9,277,868 B2* | 3/2016 | Borgos | A61B 5/022 |
| 9,282,931 B2* | 3/2016 | Tearney | A61B 1/00082 |
| 9,326,711 B2 | 5/2016 | Kracker et al. | |
| 9,510,758 B2* | 12/2016 | Warger, II | A61B 5/0066 |
| 9,596,990 B2* | 3/2017 | Park | H04W 4/027 |
| 9,603,524 B2* | 3/2017 | Park | A61B 5/0002 |
| 9,636,041 B2* | 5/2017 | Zalevsky | A61B 5/14532 |
| 9,668,672 B2* | 6/2017 | Zalevsky | A61B 5/14532 |
| 9,704,050 B2* | 7/2017 | Lee | G06K 9/00577 |
| 10,357,165 B2* | 7/2019 | Yoon | A61B 5/681 |
| 2002/0007125 A1 | 1/2002 | Hickey | |
| 2002/0095092 A1 | 7/2002 | Kondo et al. | |
| 2003/0013976 A1 | 1/2003 | Freund et al. | |
| 2004/0186387 A1 | 9/2004 | Kosuda et al. | |
| 2005/0228297 A1 | 10/2005 | Banet et al. | |
| 2007/0078308 A1 | 4/2007 | Daly | |
| 2007/0163353 A1 | 7/2007 | Lec et al. | |
| 2007/0265533 A1 | 11/2007 | Tran | |
| 2007/0276262 A1 | 11/2007 | Banet et al. | |
| 2007/0276632 A1 | 11/2007 | Banet et al. | |
| 2008/0071180 A1* | 3/2008 | Borgos | A61B 5/022 600/500 |
| 2008/0146952 A1* | 6/2008 | Presura | A61B 5/02444 600/508 |
| 2008/0181556 A1* | 7/2008 | Borgos | A61B 5/022 385/13 |
| 2008/0183053 A1* | 7/2008 | Borgos | A61B 5/022 600/301 |
| 2008/0228089 A1 | 9/2008 | Cho et al. | |
| 2009/0069698 A1 | 3/2009 | Bae et al. | |
| 2009/0073461 A1* | 3/2009 | Borgos | A61B 5/022 356/622 |
| 2009/0209834 A1* | 8/2009 | Fine | A61B 5/14551 600/316 |
| 2009/0209871 A1 | 8/2009 | Ueki et al. | |
| 2009/0326393 A1 | 12/2009 | Sethi et al. | |
| 2010/0022861 A1 | 1/2010 | Cinbis et al. | |
| 2010/0049059 A1 | 2/2010 | Ha et al. | |
| 2010/0145171 A1 | 6/2010 | Park et al. | |
| 2010/0160798 A1 | 6/2010 | Banet et al. | |
| 2010/0168589 A1 | 7/2010 | Banet et al. | |
| 2010/0210930 A1 | 8/2010 | Saylor | |
| 2010/0210956 A1 | 8/2010 | Im | |
| 2010/0324384 A1 | 12/2010 | Moon et al. | |
| 2011/0021931 A1* | 1/2011 | Borgos | A61B 5/022 600/490 |
| 2011/0172505 A1 | 7/2011 | Kim et al. | |
| 2011/0208066 A1 | 8/2011 | Gnadinger | |
| 2012/0025185 A1 | 2/2012 | Kasamatsu | |
| 2012/0108956 A1* | 5/2012 | Warger, II | A61B 5/0066 600/425 |
| 2012/0130215 A1* | 5/2012 | Fine | A61B 5/02241 600/369 |
| 2012/0130253 A1 | 5/2012 | Nadkarni et al. | |
| 2012/0130260 A1* | 5/2012 | Borgos | A61B 5/022 600/490 |
| 2012/0136261 A1 | 5/2012 | Sethi et al. | |
| 2012/0143066 A1 | 6/2012 | Antonelli et al. | |
| 2012/0191001 A1 | 7/2012 | Segman | |
| 2013/0046192 A1 | 2/2013 | Lin et al. | |
| 2013/0131475 A1* | 5/2013 | Eisen | A61B 5/14552 600/324 |
| 2013/0144137 A1 | 6/2013 | Zalevsky et al. | |
| 2013/0190630 A1 | 7/2013 | Borgos | |
| 2013/0218025 A1 | 8/2013 | Tverskoy | |
| 2013/0245456 A1 | 9/2013 | Ferguson, Jr. et al. | |
| 2014/0012146 A1 | 1/2014 | Fukuda | |
| 2014/0066788 A1 | 3/2014 | Mukkamala et al. | |
| 2014/0066793 A1 | 3/2014 | Mukkamala et al. | |
| 2014/0081153 A1 | 3/2014 | Kuno | |
| 2014/0107493 A1* | 4/2014 | Yuen | H04W 4/027 600/473 |
| 2014/0125491 A1* | 5/2014 | Park | H04W 4/027 340/870.01 |
| 2014/0127996 A1* | 5/2014 | Park | H04W 4/027 455/41.1 |
| 2014/0148658 A1 | 5/2014 | Zalevsky et al. | |
| 2014/0200423 A1* | 7/2014 | Eisen | A61B 5/14551 600/340 |
| 2014/0288435 A1 | 9/2014 | Richards et al. | |

(56) References Cited

U.S. PATENT DOCUMENTS

| | | | |
|---|---|---|---|
| 2015/0105638 A1* | 4/2015 | Eisen | A61B 5/14552 600/324 |
| 2015/0117015 A1 | 4/2015 | Roh et al. | |
| 2015/0119725 A1 | 4/2015 | Martin et al. | |
| 2015/0126820 A1 | 5/2015 | Muhlsteff | |
| 2015/0323311 A1* | 11/2015 | Muijs | G01B 11/162 356/28.5 |
| 2016/0058300 A1 | 3/2016 | Yoon et al. | |
| 2016/0066790 A1* | 3/2016 | Shcherbakov | A61B 5/0059 356/511 |
| 2016/0081572 A1 | 3/2016 | Hong et al. | |
| 2016/0103985 A1 | 4/2016 | Shim et al. | |
| 2016/0106325 A1* | 4/2016 | Kang | A61B 5/0261 600/480 |
| 2016/0106327 A1 | 4/2016 | Yoon et al. | |
| 2016/0106333 A1* | 4/2016 | Kang | A61B 5/0059 600/301 |
| 2016/0113589 A1 | 4/2016 | Yoon | |
| 2016/0157736 A1* | 6/2016 | Huang | A61B 5/0059 600/477 |
| 2016/0192845 A1* | 7/2016 | Warger | A61B 5/0066 600/301 |
| 2016/0198961 A1* | 7/2016 | Homyk | A61B 5/0082 600/476 |
| 2016/0206251 A1 | 7/2016 | Kwon et al. | |
| 2016/0256116 A1 | 9/2016 | Baik et al. | |
| 2016/0256117 A1 | 9/2016 | Baik et al. | |
| 2016/0278645 A1 | 9/2016 | Yoon | |
| 2016/0278718 A1* | 9/2016 | Fujii | A61B 3/1233 |
| 2016/0287109 A1 | 10/2016 | Shim et al. | |
| 2016/0357154 A1 | 12/2016 | Shim et al. | |
| 2017/0017858 A1* | 1/2017 | Roh | G06T 7/20 |
| 2017/0049340 A1 | 2/2017 | Cho et al. | |
| 2017/0055855 A1 | 3/2017 | Yoon | |
| 2017/0065184 A1 | 3/2017 | Barak | |
| 2017/0105679 A1 | 4/2017 | Gil | |
| 2017/0112395 A1* | 4/2017 | Kim | A61B 5/02125 |
| 2017/0135636 A1* | 5/2017 | Park | A61B 5/681 |
| 2017/0150930 A1* | 6/2017 | Shikii | A61B 5/7278 |
| 2017/0172510 A1* | 6/2017 | Homyk | A61B 5/721 |
| 2017/0209047 A1* | 7/2017 | Zalevsky | A61B 3/165 |
| 2017/0245796 A1 | 8/2017 | Zalesky et al. | |
| 2017/0251926 A1 | 9/2017 | Yoon et al. | |
| 2017/0319146 A1 | 11/2017 | Park et al. | |

FOREIGN PATENT DOCUMENTS

| | | |
|---|---|---|
| DE | 102010014761 A1 | 10/2011 |
| EP | 0755221 B1 | 10/2001 |
| EP | 1 204 370 B1 | 4/2008 |
| EP | 3072441 A1 | 9/2016 |
| JP | 11-155826 A | 6/1999 |
| JP | 2000-166885 A | 6/2000 |
| JP | 2003-532478 A | 11/2003 |
| JP | 3769524 B2 | 4/2006 |
| JP | 2008-295576 A | 12/2008 |
| JP | 4506849 B2 | 7/2010 |
| JP | 4614184 B2 | 1/2011 |
| JP | 4645259 B2 | 3/2011 |
| JP | 4848732 B2 | 12/2011 |
| JP | 2012-57962 A | 3/2012 |
| JP | 2012-161507 A | 8/2012 |
| JP | 2012-187300 A | 10/2012 |
| JP | 2012202776 A | 10/2012 |
| JP | 2013-509225 A | 3/2013 |
| JP | 2014-23031 A | 2/2014 |
| JP | 5528816 B2 | 6/2014 |
| JP | 2014240782 A | 12/2014 |
| JP | 2015502197 A | 1/2015 |
| KR | 10-0610813 B1 | 8/2006 |
| KR | 10-0650044 B1 | 11/2006 |
| KR | 10-2008-0073988 A | 8/2008 |
| KR | 10-2009-0052442 A | 5/2009 |
| KR | 10-2010-0060141 A | 6/2010 |
| KR | 10-2010-0065084 A | 6/2010 |
| KR | 10-1007354 B1 | 1/2011 |
| KR | 1020110025100 A | 3/2011 |
| KR | 10-1040598 B1 | 6/2011 |
| KR | 10-1058152 B1 | 8/2011 |
| KR | 10-1065615 B1 | 9/2011 |
| KR | 10-2012-0057813 A | 6/2012 |
| KR | 10-1310464 B1 | 9/2013 |
| KR | 10-2014-0024845 A | 3/2014 |
| KR | 10-1503604 B1 | 3/2015 |
| KR | 10-1564066 B1 | 10/2015 |
| KR | 101560287 B1 | 10/2015 |
| KR | 10-2016-0041553 A | 4/2016 |
| KR | 10-2016-0088127 A | 7/2016 |
| KR | 10-2016-0107007 A | 9/2016 |
| KR | 10-2016-0108081 A | 9/2016 |
| KR | 1020170104361 A | 9/2017 |
| KR | 1020170124943 A | 11/2017 |
| WO | 2015129949 A1 | 9/2015 |

OTHER PUBLICATIONS

Yan et al; "Noninvasive Estimation of Blood Pressure Using Photophlethysmographic Signals in the Period Domain"; Proceedings of the 2005 IEEE Engineering in Medicine and Biology 27th Annual Conference; Sep. 1-4, 2005; 2 pgs. total.

Fortino et al; "PPG-based Methods for Non Invasive and Continuous Blood Pressure Measurement: an Overview and Development Issues in Body Sensor Networks"; IEEE; 2010; 4 pgs. total.

Kurylyak, et al; "A Neural Network-based Method for Continuous Blood Pressure Estimation from a PPG Signal"; Instrumentation and Measurement Technology Conference (I2MTC); May 6-9, 2013; 4pgs. Total, pp. 280-283.

Teng et al; "Continuous and Noninvasive Estimation of Arterial Blood Pressure Using Photoplethysmographic Approach"; Proceedings of the 25th Annual International Conference of the IEEE EMBS; Sep. 17-21, 2003; 4 pgs. Total, pp. 3153-3156.

Young-Zoon Yoon.," Study on cardiovascular system with blood pressure waveform and heart rate variability", A Dissertation Submitted to the Faculty of Seoul National University in Partial Fulfillment of the Requirements for the Degree of Doctor of Philosophy, School of Physics, Graduate School, Seoul National University, 2005, (210 Pages Total).

Chen et al., "Estimation of Central Aortic Pressure Waveform by Mathematical Transformation of Radial Tonometry Pressure; Validation of Generalized Transfer Function", 1997: 95, 1827-36, 12 pages total, American Heart Association.

O'Rourke et al., "Pulse wave analysis", Research Methods in Human Cardiovascular Pharmacology, 2001, Clinical Pharmacology, Blackwell Science Ltd Br J Clin Pharmacol: 51, pp. 507-522, 16 pages total.

Aymen A. Awad et al., "How Does the Plethysmogram Derived from the Pulse Oximeter Relate to Arterial Blood Pressure in Coronary Artery Bypass Graft Patients?"; Anesth Analg, 93; 2001; pp. 1466-1471; 6 pgs. total.

Satomi Suzuki, et al., "Cuffless and Non-invasive Systolic Blood Pressure Estimation for Aged Class by Using Photoplethysmograph"; 30th Annual International IEEE EMBS Conference; Aug. 20-24, 2008; pp. 1327-1330; 4 pgs. total.

Arata Suzuki et al., "Feature Selection Method for Estimating Systolic Blood Pressure Using the Taguchi Method"; IEEE Transactions on Industrial Informatics; vol. 10; No. 2; May 2014; pp. 1077-1085; 9 pgs. total.

Y. Kurylyak et al., "Photoplethysmogram-based Blood Pressure Evaluation using Kalman Filtering and Neural Networks"; Medical Measurements and Applications Proceedings (MeMeA), 2013 IEEE International Symposium; May 4, 2013; 5 pgs. total.

Yevgeny Beiderman et al., "Remote estimation of blood pulse pressure via temporal tracking of reflected secondary speckles pattern"; Journal of Biomedical Optics; vol. 15; No. 6; Nov./Dec. 2010; pp. 061707-1-061707-7; 7 pgs. total.

Yu.N. Kul'Chin et al., "Correlation method for processing speckles of signals from single-fibre multimode interferometers by using

(56) References Cited

OTHER PUBLICATIONS charge-coupled devices"; Optical Fibres and Waveguides; Quantum Electronics; vol. 36; No. 4; 2006; pp. 339-342; 5 pgs. total.
Enric Monte-Moreno., "Non-invasive estimate of blood glucose and blood pressure from a photoplethysmograph by means of machine learning techniques", Artificial Intelligence in Medicine, vol. 53, 2011, pp. 127-138, 12 Pages total.
Communication dated Aug. 30, 2016 issued by the European Patent Office in counterpart European Patent Application No. 16158751.4.
Ramakrishna Mukkamala et al., "Towards Ubiquitous Blood Pressure Monitoring via Pulse Transit Time: Theory and Practice", IEEE Trans Biomed Eng. Aug. 2015 ; 62(8), pp. 1879-1901, 48 pages total.
Qing Liu et al., "Attenuation of Systolic Blood Pressure and Pulse Transit Time Hysteresis During Exercise and Recovery in Cardiovascular Patients", IEEE Transactions on Biomedical Engineering, vol. 61, No. 2, Feb. 2014, pp. 346-352.
R. A. Payne et al., "Pulse transit time measured from the ECG: an unreliable marker of beat-to-beat blood pressure", J Appl Physiol, the American Physiological Society 100, 2006, pp. 136-141.
Office Action dated Mar. 20, 2017 issued by United States Patent and Trademark Office, in U.S. Appl. No. 14/818,420.
Office Action dated Jun. 16, 2017 issued by the United States Patent and Trademark Office, in U.S. Appl. No. 14/818,420.
Office Action dated Apr. 17, 2017 issued by the United States Patent and Trademark Office, in U.S. Appl. No. 15/068,760.
Jianjun Qiu et al; "Spatiotemporal laser speckle contrast analysis for blood flow imaging with maximized speckle contrast"; Journal of Biomedical Optics; vol. 15; No. 1; Jan./Feb. 2010; pp. 016003-1-016003-5; 5pgs. total.
Dr. S. Shah et al; "Optoelectronic blood pressure estimation: A novel principle for blood pressure measurement"; Tarilian Laser Technologies; (http://www.tarilian-lasertechnologies.com/press/tlt-at-esh2012.php); 2012; 4 pgs. total.
"Tarilian Laser Technologies achieves greatest technological advance in blood pressure measurement for 130 years"; (http://vvww.tarilian-lasertechnologies.com/press/pr111201.php); Tarilian Laser Technologies; Dec. 7, 2011; 6 pgs. total.
Communication dated Dec. 14, 2017, issued by the European Patent Office in counterpart European Application No. 17172684.7.
Office Action dated Feb. 15, 2019 issued by the U.S. Patent and Trademark Office in U.S. Appl. No. 14/961,145.
Notice of Allowance dated Mar. 4, 2019 issued by the U.S. Patent and Trademark Office in U.S. Appl. No. 14/818,420.
Final Office Action dated Mar. 7, 2019 issued by the U.S. Patent and Trademark Office in U.S. Appl. No. 14/833,221.
Notice of Allowance dated Mar. 18, 2019 issued by the U.S. Patent and Trademark Office in U.S. Appl. No. 15/068,760.
Non-Final Office Action dated Mar. 22, 2019 issued by the U.S. Patent and Trademark Office in U.S. Appl. No. 14/862,288.
Final Office Action dated Sep. 26, 2017 issued by the U.S. Patent and Trademark Office in U.S. Appl. No. 15/068,760.
U.S. Non-Final Office Action dated Sep. 27, 2017 issued by the U.S. Patent and Trademark Office in U.S. Appl. No. 14/961,145.
U.S. Non-Final Office Action dated Nov. 1, 2017 issued by the U.S. Patent and Trademark Office in U.S. Appl. No. 14/862,288.
U.S. Non-Final Office Action dated Dec. 22, 2017 issued by the U.S. Patent and Trademark Office in U.S. Appl. No. 14/818,420.
U.S. Non-Final Office Action dated Jan. 30, 2018 by the U.S. Patent and Trademark Office in U.S. Appl. No. 15/068,760.
U.S. Final Office Action dated Feb. 28, 2018 by the U.S. Patent and Trademark Office in U.S. Appl. No. 14/961,145.
Restriction Requirement dated Mar. 8, 2018 by the U.S. Patent and Trademark Office in U.S. Appl. No. 14/833,221.
U.S. Final Office Action dated May 23, 2018 by U.S. Patent and Trademark Office, in U.S. Appl. No. 14/862,288.
U.S. Non-Final Office Action dated May 25, 2018 by U.S. Patent and Trademark Office, in U.S. Appl. No. 14/961,145.
U.S. Final Office Action dated Jul. 16, 2018 by the U.S. Patent and Trademark Office in U.S. Appl. No. 15/068,760.
U.S. Non-Final Office Action dated Jul. 26, 2018 by the U.S. Patent and Trademark Office in U.S. Appl. No. 14/833,221.
U.S. Advisory Action dated Aug. 2, 2018 by the U.S. Patent and Trademark Office in U.S. Appl. No. 14/862,288.
U.S. Final Office Action dated Aug. 6, 2018 by the U.S. Patent and Trademark Office in U.S. Appl. No. 14/818,420.
Restriction Requirement dated Sep. 6, 2018 issued by the U.S. Patent and Trademark Office in U.S. Appl. No. 14/884,019.
Notice of Allowance dated Oct. 24, 2018, issued by United States Patent and Trademark Office in U.S. Appl. No. 15/068,760.
Notice of Allowance dated Nov. 15, 2018, issued by United States Patent and Trademark Office in U.S. Appl. No. 14/818,420.
U.S. Non-Final Office dated Dec. 14, 2018 issued by the U.S. Patent and Trademark Office in U.S. Appl. No. 14/884,019.
Restriction Requirement dated Jan. 14, 2019 issued by the U.S. Patent and Trademark Office in U.S. Appl. No. 15/654,422.
Advisory Action dated Dec. 19, 2017 issued by the U.S. Patent and Trademark Office in U.S. Appl. No. 15/068,760.
Anonymous, "Central Venous Pressure Waveforms", Section 3: Anesthesia Management, Part B: Monitoring, Chapter 30: Cardiovascular Monitoring, 1979, http://web.squ.edu.om/med-Lib/MED_CD/E_CDs/anesthesia/site/content/v03/030275r00.HTM; 4 pages total.
Notice of Allowance dated Jul. 31, 2019 issued by the USPTO in U.S. Appl. No. 14/862,288.
Notice of Allowance dated Apr. 24, 2019 issued by the U.S. Patent and Trademark Office in U.S. Appl. No. 14/961,145.
Non-Final Office Action dated Apr. 26, 2019 issued by the U.S. Patent and Trademark Office in U.S. Appl. No. 15/654,422.
Office Action dated Jun. 20, 2019, issued by the U.S. Patent and Trademark Office in U.S. Appl. No. 14/884,019.
Wilson et al., "The Potential Variations Produced by the Heart Beat at the Apices of Einthoven's Triangle". American Heart Journal, vol. 7, issue 2, 1931, 6 pages total.
Office Action dated Sep. 27, 2019 issued by the United States Patent and Trademark Office in counterpart U.S. Appl. No. 15/654,422.
Advisory Action dated Dec. 12, 2019 issued by the U.S. Patent and Trademark Office in U.S. Appl. No. 15/654,422.
Non-Final Office Action dated Jan. 10, 2020 issued by the U.S. Patent and Trademark Office in U.S. Appl. No. 14/833,221.

* cited by examiner

FIG. 11A-A
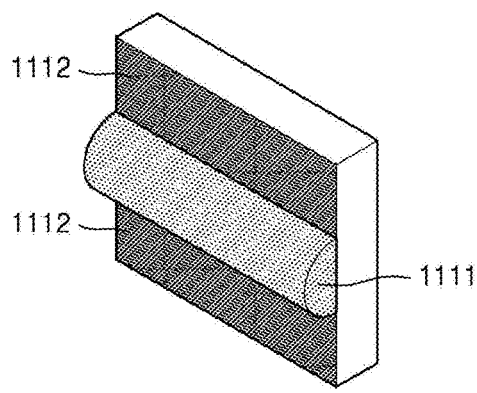
FIG. 11A-B
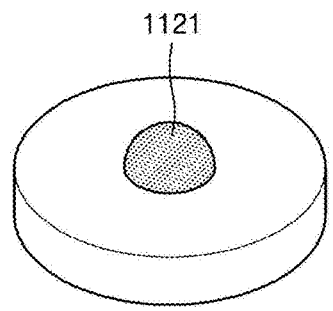
FIG. 11A-C
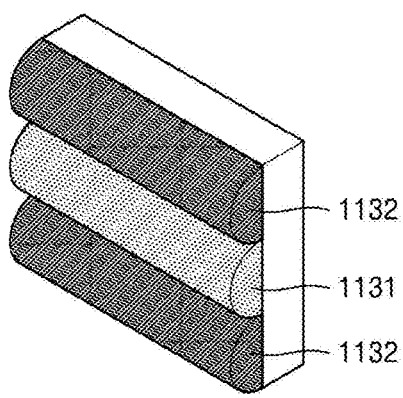
FIG. 11A-D
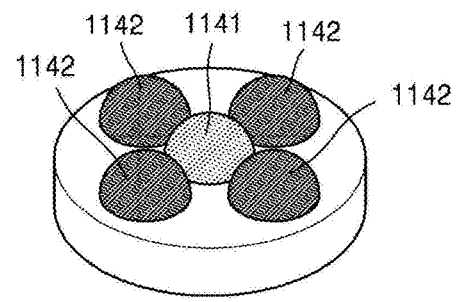

FIG. 11B-A
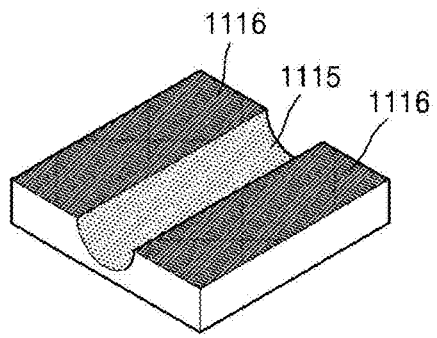
FIG. 11B-B
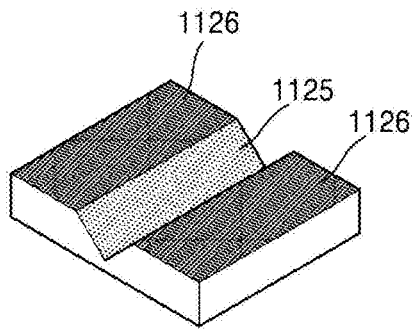
FIG. 11B-C
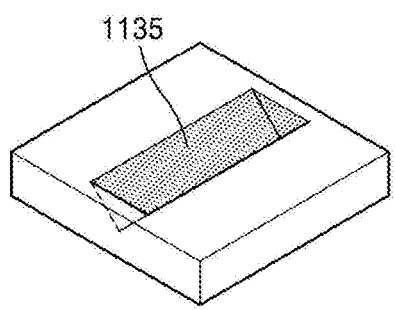
FIG. 11B-D
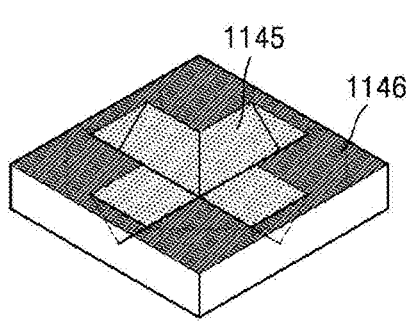
FIG. 11B-E
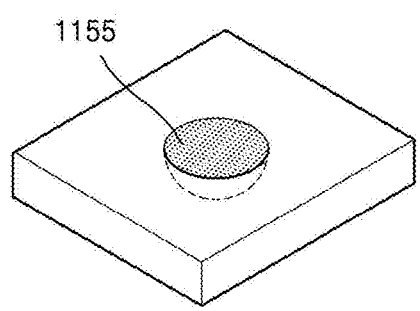
FIG. 11B-F
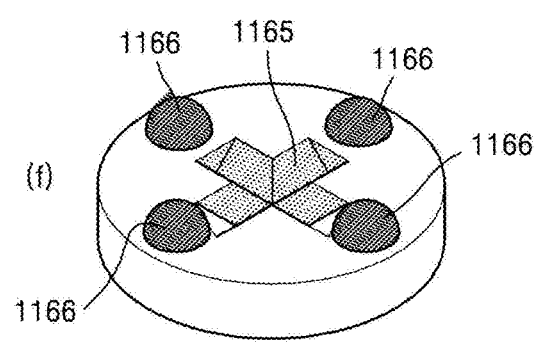
FIG. 11B-G
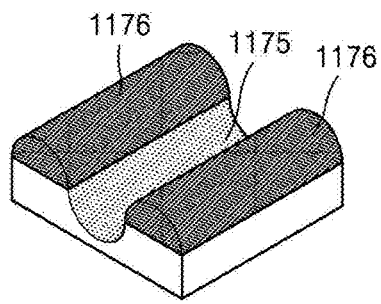

APPARATUS FOR AND METHOD OF MONITORING BLOOD PRESSURE AND WEARABLE DEVICE HAVING FUNCTION OF MONITORING BLOOD PRESSURE

CROSS-REFERENCE TO RELATED APPLICATIONS

This application claims priority from Korean Patent Application No. 10-2014-0117254, filed on Sep. 3, 2014, in the Korean Intellectual Property Office, the disclosure of which is incorporated herein by reference in its entirety.

BACKGROUND

1. Field

Apparatuses and methods consistent with exemplary embodiments relate to apparatuses for and methods of monitoring blood pressure and wearable devices having functions of monitoring blood pressure.

2. Description of the Related Art

Blood pressure is used as a measure of health. Sphygmomanometers are commonly used in medical institutions and homes for measuring blood pressure. The Food and Drug Administration (FDA) of the United States requires that sphygmomanometers meet standards required by the Association for the Advancement of Medical Instrumentation (AAMI). The ANSI/AAMI SP10 Report issued by the AAMI suggests standards for labeling, safety, and performance requirements of a sphygmomanometer. When a cuff-type sphygmomanometer is used, a systolic blood pressure and a diastolic blood pressure are measured by placing a cuff around a body part through which arterial blood flows, inflating the cuff until the artery is occluded, and then slowly releasing the pressure in the cuff. However, the cuff-type sphygmomanometer is quite large to carry, and thus it is quite inconvenient to continuously monitor a change in the blood pressure of a person in real time by using the cuff-type sphygmomanometer. Accordingly, a great deal of research on cuffless sphygmomanometers for measuring blood pressure has recently been made.

SUMMARY

Exemplary embodiments of the present application relate to of monitoring blood pressure and wearable devices having functions of monitoring blood pressure. Additional aspects of the exemplary embodiments will be set forth in part in the description which follows and, in part, will be apparent from the description, or may be learned by practice of the presented exemplary embodiments.

According to an aspect of an exemplary embodiment, there is provided an apparatus for monitoring a blood pressure including: a laser emitter configured to emit a laser towards a blood vessel in a body part; a speckle detector configured to detect, from the body part, laser speckles caused by scattering of the emitted laser and reflected from the body part; and a controller configured to obtain a bio-signal indicating a change in a volume of the blood vessel from the laser speckles and estimate the blood pressure based on the obtained bio-signal.

The controller may be configured to obtain the bio-signal by analyzing a speckle fluctuation of the laser speckles, the speckle fluctuation corresponding to the change in the volume of the blood vessel.

The obtained bio-signal may include a photoplethysmogram (PPG) signal obtained based on a correlation between the analyzed speckle fluctuation and the change in the volume of the blood vessel.

The controller may be configured to obtain the bio-signal based on a relationship between an intensity of an optical signal received by the speckle detector and time.

The speckle detector may include at least one photodetecting device for detecting the laser speckles.

The speckle detector may include a plurality of the photodetecting devices, and the controller may be configured to estimate the blood pressure based on laser speckles that is detected by at least one of the plurality of photodetecting devices.

The controller may include: a selector configured to select at least one photodetecting device from among the plurality of photodetecting devices based on a detection sensitivity of each of the plurality of photodetecting devices; and a blood pressure estimator configured to estimate the blood pressure based on the laser speckles that is detected by the selected at least one photodetecting device.

The controller may include: a bio-signal analyzer configured to convert a change in an intensity of an optical signal corresponding to the speckle fluctuation of the laser speckles which is detected for a predetermined period of time after the laser is emitted into a photoplethysmogram (PPG) signal; and a blood pressure estimator configured to estimate a systolic blood pressure and a diastolic blood pressure based on waveform characteristics of the PPG signal.

The laser emitter may include at least one laser diode device configured to oscillate the laser, and the speckle detector may include a plurality of photodetecting devices configured to detect the laser speckles, wherein the at least one laser diode device and the plurality of photodetecting devices are packaged on a common substrate.

Each of the plurality of photodetecting devices may be packaged on the common substrate and at a same distance from the at least one laser diode device.

The plurality of photodetecting devices may be symmetrically spaced from the at least one laser diode device.

A second substrate stacked on the common substrate may include at least one selected from a first lens through which the emitted laser passes and a second lens through which a laser reflected from the laser speckles passes, and a surface into which the first lens and the second lens are not inserted and which is anti-reflection (AR) coated.

Each of the first lens and the second lens may include at least one selected from a cylindrical lens and a flat lens.

The emitted laser and the reflected laser corresponding to the laser speckles may be in a same wavelength band.

According to an aspect of an exemplary embodiment, a wearable device configured to monitor a blood pressure may include: at least one blood pressure monitoring module configured to measure a blood pressure of a user; a user interface module configured to provide information about the blood pressure; and a processor that controls the at least one blood pressuring monitoring module and the user interface module, wherein each of the at least one blood pressure monitoring module includes: a laser emitter configured to emit a laser towards a blood vessel in a body part; a speckle detector configured to detect laser speckles caused by scattering of the emitted laser and reflected from the body part; and a controller configured to obtain a bio-signal indicating a change in a volume of the blood vessel from the detected laser speckles and estimate the blood pressure based on the obtained bio-signal.

The controller may be further configured to obtain the bio-signal by analyzing a speckle fluctuation of the laser speckles, the speckle fluctuation corresponding to the change in the volume of the blood vessel and being analyzed based on a relationship between an intensity of an optical signal that is received by the speckle detector and time.

The wearable device may include a wristwatch-type device that is configured to be worn on a wrist of the user, and the blood vessel may be a radial artery in the wrist.

The wearable device may include a plurality of the blood pressure monitoring modules, and may be configured to estimate the blood pressure by using all or some of the plurality of blood pressure monitoring modules according to a monitoring sensitivity of each of the plurality of blood pressure monitoring modules.

According to an aspect of another exemplary embodiment, a method of monitoring a blood pressure includes: emitting a laser towards a blood vessel in a body part; detecting, from the body part, laser speckles caused by scattering of the emitted laser and reflected from the body part; obtaining a bio-signal indicating a change in a volume of the blood vessel from the detected laser speckles; and estimating the blood pressure based on the obtained bio-signal.

The step of obtaining a bio-signal may be performed by analyzing a speckle fluctuation of the laser speckles, the speckle fluctuation corresponding to the change in the volume of the blood vessel and analyzed based on a relationship between an intensity of an optical signal that is received by a speckle detector and time.

The method may further include selecting at least one photodetecting device from a plurality of photodetecting devices of a speckle detector based on a detection sensitivity of each of the plurality of photodetecting devices, wherein the step of estimating a blood pressure is performed based on laser speckles that is detected by the selected at least one photodetecting device.

The step of obtaining a bio-signal may be performed by converting a change in an intensity of an optical signal corresponding to a speckle fluctuation of the laser speckles which is detected for a predetermined period of time after the laser is emitted into a photoplethysmogram (PPG) signal, and the step of estimating a blood pressure may include estimating a systolic blood pressure and a diastolic blood pressure based on waveform characteristics of the PPG signal.

BRIEF DESCRIPTION OF THE DRAWINGS

The above and other aspects of the exemplary embodiments will become apparent and more readily appreciated from the following description of the exemplary embodiments, taken in conjunction with the accompanying drawings in which:

FIGS. 11A-A, 11A-B, 11A-C and 11A-D illustrate various examples of a transparent substrate that may be stacked on a circuit board, according to an exemplary embodiment;

FIGS. 11B-A, 11B-B, 11B-C, 11B-D, 11B-E, 11B-F, and 11B-G illustrate various examples of a transparent substrate that may be stacked on a circuit board, according to an exemplary embodiment;

DETAILED DESCRIPTION

Most of the terms used herein are general terms that have been widely used in the technical art to which the inventive concept pertains. However, some of the terms used herein may be created reflecting intentions of technicians in this art, precedents, or new technologies. Also, some of the terms used herein may be arbitrarily chosen by the present applicant. In this case, these terms are defined in detail below. Accordingly, the specific terms used herein should be understood based on the unique meanings thereof and the whole context of the inventive concept.

Throughout the specification, it will be understood that when an element is referred to as being "connected" to another element, it may be "directly connected" to the other element or "electrically connected" to the other element with intervening elements therebetween. It will be further understood that when a part "includes" or "comprises" an element, unless otherwise defined, the part may further include other elements, not excluding the other elements. Also, the terms, such as 'unit' or 'module', should be understood as a unit that processes at least one function or operation and that may be embodied in a hardware manner, a software manner, or a combination of the hardware manner and the software manner.

The terms "configured" or "included" used herein should not be construed to include all of various elements or steps described in the specification, and should be construed to not include some of the various elements or steps or to further include additional elements or steps.

Also, it will be understood that although the terms "first", "second", etc. may be used herein to describe various elements, these elements should not be limited by these terms. These elements are only used to distinguish one element from another.

Aspects of the present application will become more apparent to one of ordinary skill in the art by describing in detail exemplary embodiments thereof with reference to the accompanying drawings. The exemplary embodiments may have different forms and should not be construed as being limited to the descriptions set forth herein. Accordingly, any feature which may be easily derived by one of ordinary skill in the art from the detailed description and the embodiments is construed as being included in the scope of the present disclosure.

As used herein, the term "and/or" includes any and all combinations of one or more of the associated listed items. Expressions such as "at least one of," when preceding a list of elements, modify the entire list of elements and do not modify the individual elements of the list.

Figure 1B:
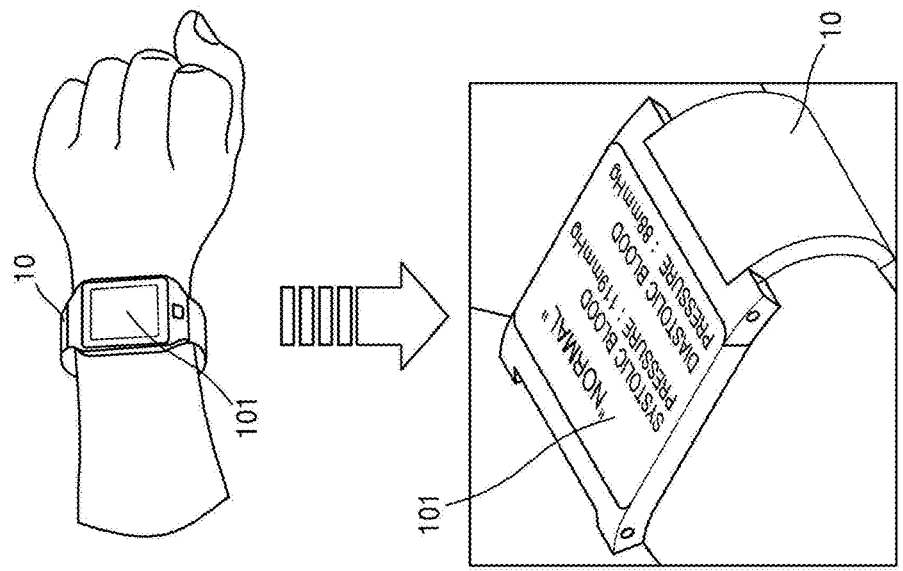
FIGS. 1A and 1B illustrate a wearable device that may be worn on a wrist to monitor a blood pressure, according to an exemplary embodiment.
Figure 1A:
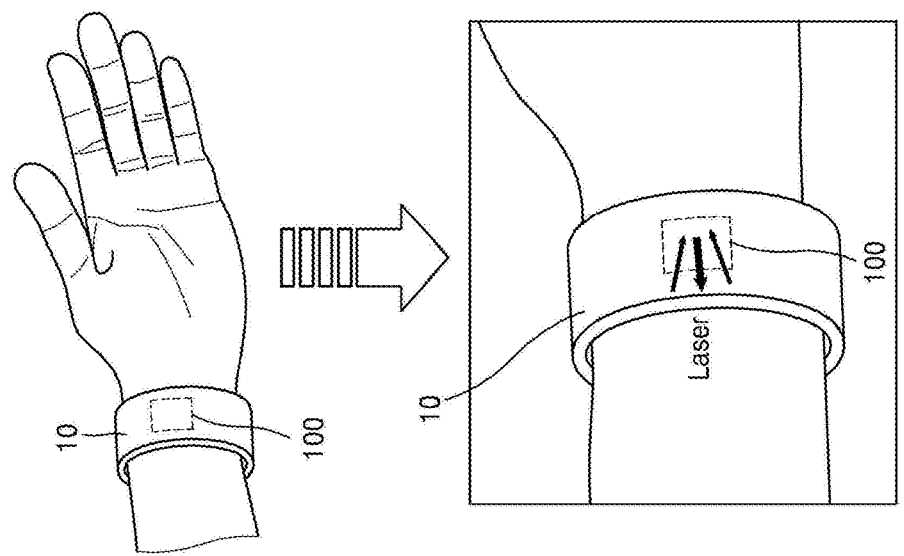

FIGS. 1A and 1B illustrate a wearable device 10 that may be worn on a wrist and may monitor a blood pressure, according to an exemplary embodiment.

Referring to FIGS. 1A and 1B, examples of the wearable device 10 may include a wristwatch-type device, a bracelet-type device, a ring-type device, a glasses-type device, and a headband-type device each having a communication function and a data processing function. Although the wearable device 10 is described as a wristwatch-type device or a wristband-type device, the exemplary embodiments are not limited thereto.

Referring to FIG. 1A, the wearable device 10 may be worn on a wrist of a user and may monitor or measure a blood pressure of the user by emitting a laser to the skin of the wrist. In detail, a blood pressure monitoring module 100 is embedded in the wearable device 10. The blood pressure monitoring module 100 that is embedded in the wearable device 10 may monitor the blood pressure of the user by emitting a laser to the skin of the wrist of the user and analyzing an optical signal corresponding to the reflection of the laser from the skin. That is, the blood pressure monitoring module 100 of the wearable device 10 may measure the blood pressure of the user by using the linearity of a laser when the blood pressure monitoring module 100 contacts the skin of the user or even when the blood pressure monitoring module 100 is slightly spaced apart from the skin of the user.

Referring to FIG. 1B, the user may receive information about the blood pressure of the user on a display screen of a user interface module 101 of the wearable device 10 that is worn on the user's wrist. Examples of the information about the blood pressure may include numerical information about a minimum blood pressure and a maximum blood pressure, numerical information about a systolic blood pressure and a diastolic blood pressure of the user, and information about whether a current blood pressure state is normal or abnormal.

Figure 2:
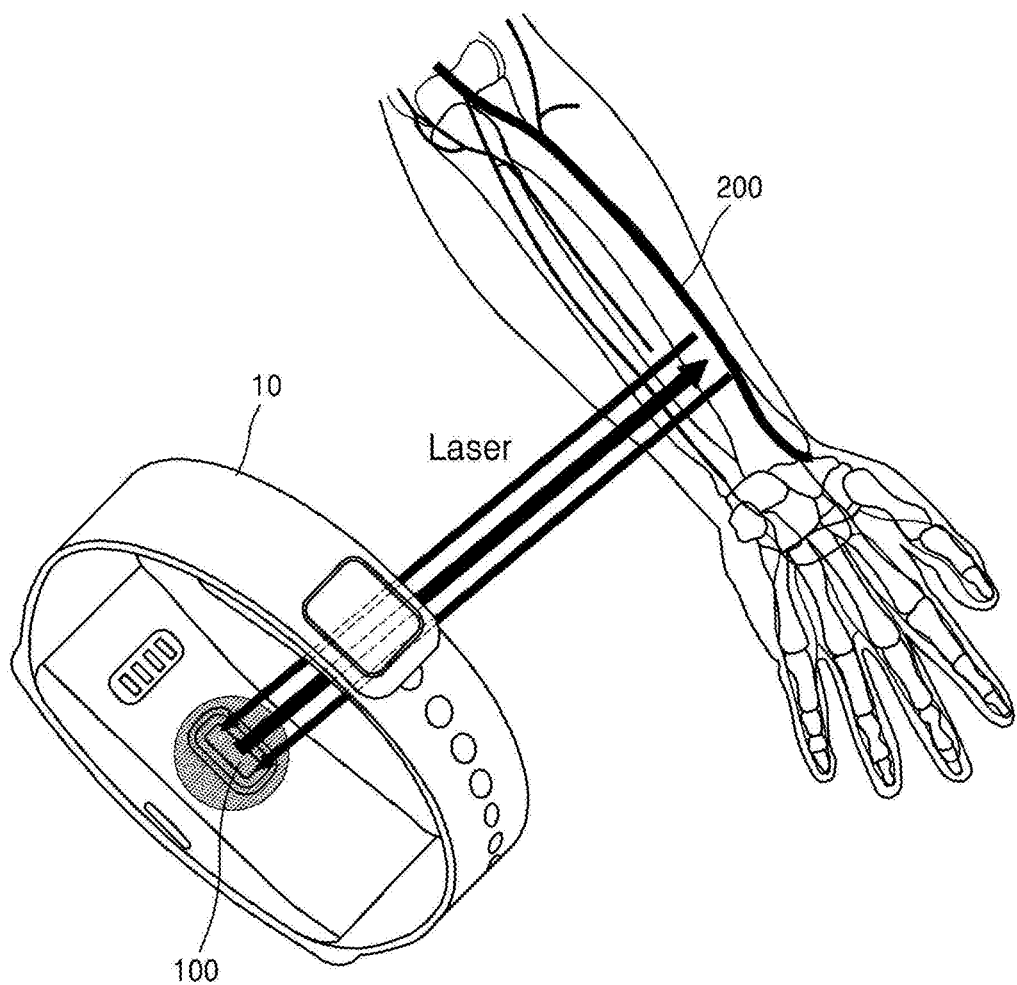
FIG. 2 illustrates using the wearable device of a wristwatch-type or wristband-type to measure a blood pressure, according to an exemplary embodiment.

FIG. 2 illustrates using the wearable device 10 that is a wristwatch-type or wristband-type device to measure a blood pressure, according to an exemplary embodiment.

Blood pressure refers to pressure that is exerted onto a wall of a blood vessel when blood sent from the heart flows in the blood vessel. Blood pressure is classified into an arterial blood pressure, a capillary blood pressure, and a venous blood pressure. An arterial blood pressure fluctuates according to a heartbeat. Also, blood pressure includes a systolic blood pressure that is a pressure when ventricles contract and blood is pushed out into an artery and a diastolic blood pressure that is a pressure when the ventricle expands and blood is not pushed out.

Referring to FIG. 2, the wearable device 10 may measure a blood pressure by emitting a laser in a contact or non-contact manner with the surface of the skin close to a radial artery 200. That is, the wearable device 10 may measure a blood pressure by emitting a laser to the radial artery 200. When a blood pressure is measured on a surface of the skin of the wrist through which the radial artery 200 passes, external factors that may cause an error in blood pressure measurement, such as the thickness of the skin tissue in the wrist, may be minimized. Also, it is known that the radial artery 200 is a blood vessel that allows a blood pressure to be more accurately measured than other blood vessels in the wrist. Accordingly, the blood pressure monitoring module 100 may be embedded in the wearable device 10 at a position at which the blood pressure monitoring module 100 may emit a laser to the radial artery 200 when the user wears the wearable device 10. However, the wearable device 10 is not limited thereto, and may measure a blood pressure by using blood vessels other than the radial artery 200, including but not limited to the brachial artery.

Figure 3:
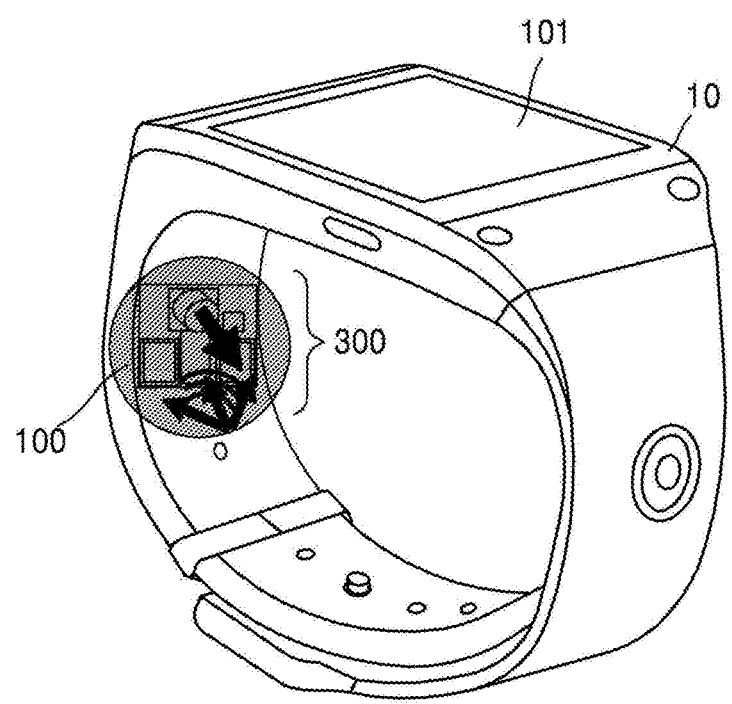
FIG. 3 illustrates a position at which a blood pressure monitoring module is embedded in the wearable device of a wristwatch-type or wristband-type, according to an exemplary embodiment.

FIG. 3 illustrates a position at which the blood pressure monitoring module 100 is embedded in the wearable device 10 that is a wristwatch-type or wristband-type device, according to an exemplary embodiment.

Referring to FIG. 3, in order to measure a blood pressure from the radial artery 200, the blood pressure monitoring module 100 may be embedded at a specific position 300 to be close to the radial artery 200 when the wearable device 10 is worn, as described above with reference to FIG. 2. However, the position at which the blood pressure monitoring module 100 is embedded in the wearable device 10 may vary according to, for example, whether the wearable device 10 is configured to be worn on the left arm or the right arm. Alternatively, the blood pressure monitoring module 100 that is embedded in the wearable device 10 may be located on a rear surface of a user interface module 101. That is, the position at which the blood pressure monitoring module 100 is embedded in the wearable device 10 is not limited to one position and may be other positions.

Figure 4:
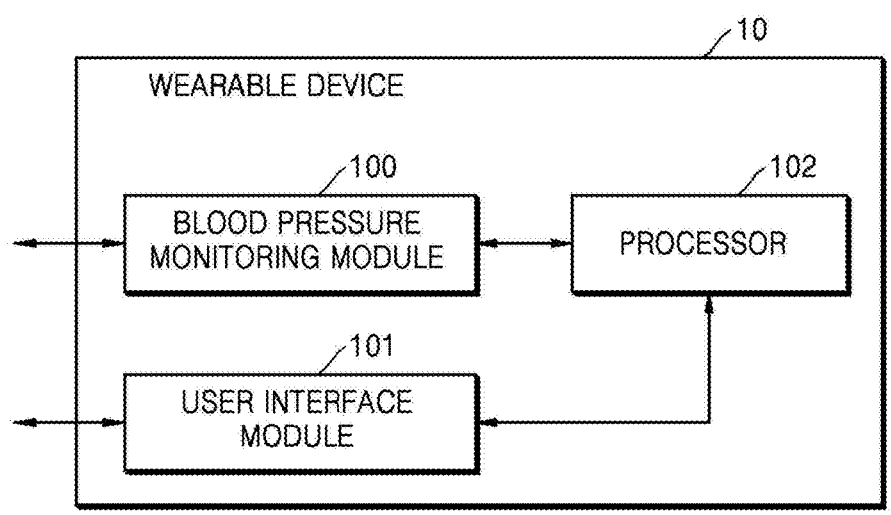
FIG. 4 is a block diagram illustrating a hardware configuration of the wearable device having a function of monitoring a blood pressure, according to an exemplary embodiment.

FIG. 4 is a block diagram illustrating a hardware configuration of the wearable device 10 having a function of monitoring a blood pressure, according to an exemplary embodiment.

Referring to FIG. 4, the wearable device 10 may include the blood pressure monitoring module 100, the user interface module 101, and a processor 102. For clarity, only certain elements of the wearable device 10 are shown in FIG. 4. Accordingly, it will be understood by one of ordinary skill in the art that the wearable device 10 may further include additional general-purpose elements other than the elements shown in FIG. 4. Although the wearable device 10 may be a wristwatch-type or wristband-type device as described above, the exemplary embodiments are not limited thereto.

The blood pressure monitoring module 100 is hardware that measures a blood pressure from a body part of the user, for example, the radial artery 200 (see FIG. 2) of the wrist. Although the blood pressure monitoring module 100 may be embedded in the wearable device 10 at the specific position 300 (see FIG. 3) of the wearable device 10 as described above, the exemplary embodiments are not limited thereto.

While the user wears the wearable device 10, the blood pressure monitoring module 100 may measure a blood pressure of the user at a specific or an arbitrary point of time, or the blood pressure monitoring module 100 may continuously monitor a blood pressure of the user.

The blood pressure monitoring module 100 may monitor a blood pressure by emitting a laser to a body part of the user and analyzing an optical signal corresponding to the reflection of the laser from the body part. The laser reflected from the body part may be an optical signal indicating laser speckles. A detailed hardware configuration, a physical structure, and an operation of the blood pressure monitoring module 100 will be explained below with reference to the drawings.

Because the blood pressure monitoring module 100 may measure a blood pressure of a body part by using a laser, the blood pressure monitoring module 100 may be classified as a sphygmomanometer using a contactless method in which the blood pressure monitoring module 100 is spaced slightly apart from the skin of the body part and measures a blood pressure by emitting a laser. Also, the blood pressure monitoring module 100 may be classified as a sphygmomanometer using a contact method in which the blood pressure monitoring module 100 is in direct contact with the skin of the body part and measures a blood pressure by emitting a laser.

Figure 20:
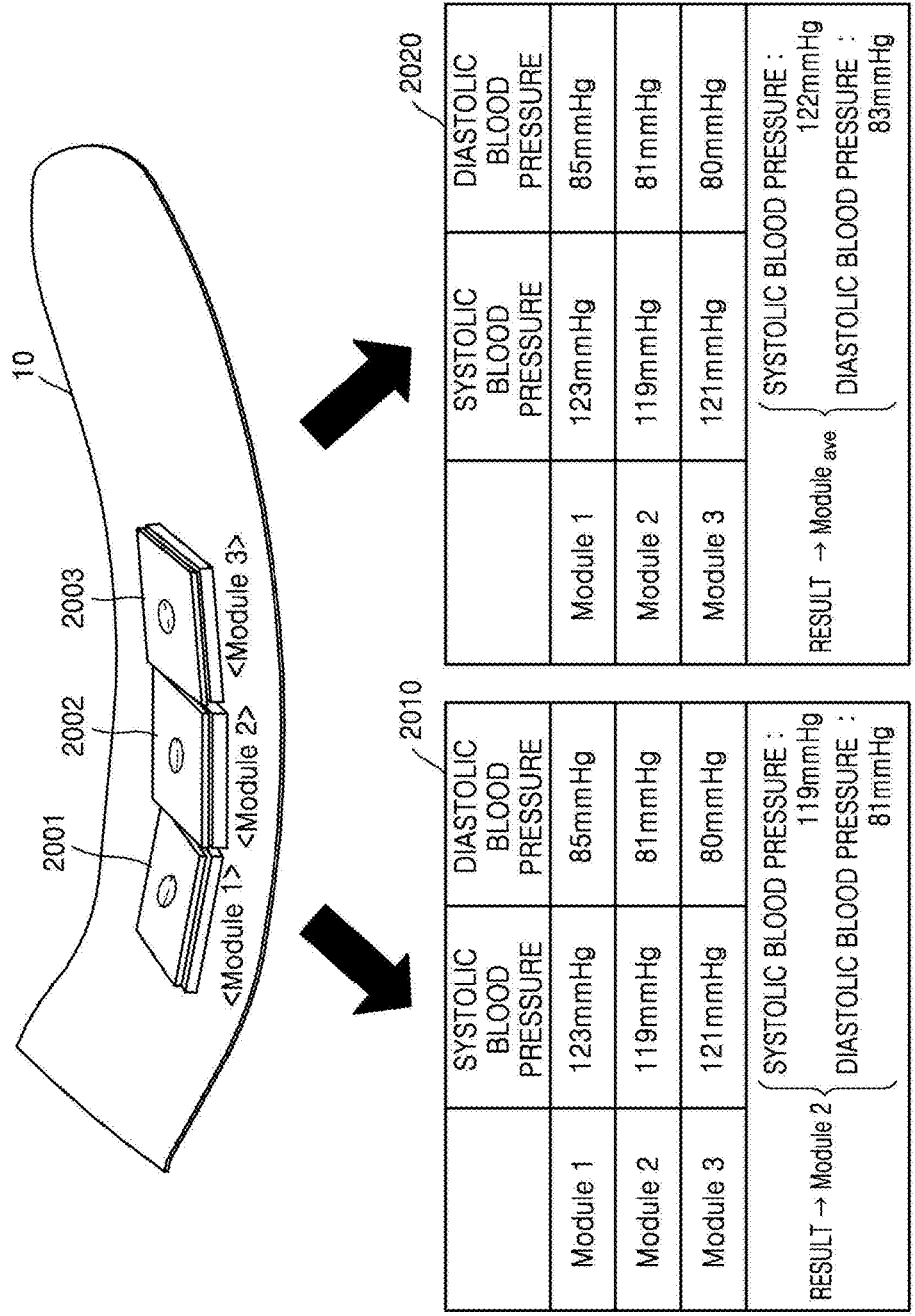
FIG. 20 illustrates a process performed by the wearable device in which a plurality of blood pressure monitoring modules are embedded to monitor a blood pressure, according to an exemplary embodiment.

Although the wearable device 10 illustrated in FIG. 4 includes only one blood pressure monitoring module 100, the exemplary embodiments are not limited thereto and the wearable device 10 may include a plurality of blood pressure monitoring modules 2001, 2002, and 2003, as shown in FIG. 20.

The user interface module 101 is hardware that provides information about a blood pressure that is monitored by the blood pressure monitoring module 100. That is, the user interface module 101 may provide to the user numerical information about a minimum blood pressure and a maximum blood pressure of the user, numerical information about a systolic blood pressure and a diastolic blood pressure of the user, or information about whether a current blood pressure state is normal or abnormal, on a display screen of the user interface module 101. Alternatively, the user interface module 101 may provide such information through an audio signal, a voice, a buzzer, or a vibration signal.

In addition to blood pressure information, the user interface module 101 may display various pieces of information that are processed by the wearable device 10. For example, when the wearable device 10 is a wristwatch-type device, the user interface module 101 may display time information. That is, the user interface module 101 may include a display unit that displays information. Also, the user interface module 101 may include an input unit that performs the function of receiving various pieces of information from the user. Although the user interface module 101 may be realized as a touch screen-type module in which a display function and an input function are combined with each other, the exemplary embodiments are not limited thereto and the user interface module 101 may be realized as a module in which a keypad and a display screen are separately provided such that the display function and the input function are separately performed.

In addition, the user interface module 101 may include various interfacing units for providing information that is processed by the wearable device 10 to the user, for example, a speaker that outputs an audio signal or a voice signal, a buzzer, or a vibration motor that outputs a vibration signal.

The processor 102 for controlling the blood pressure monitoring module 100 and the user interface module 101 may also control the overall function and operation of the wearable device 10. The processor 102 is hardware and may be realized as a single microprocessor module or a combination of two or more microprocessor modules. That is, in the exemplary embodiments, the processor 102 is not limited to one type.

According to an exemplary embodiment, when a separate microprocessor module is not included in the blood pressure monitoring module 100, the processor 102 that is provided external to the blood pressure monitoring module 100 may estimate a blood pressure by analyzing an optical signal of a laser that is detected by the blood pressure monitoring module 100. Alternatively, when a separate microprocessor module (for example, a controller 130 (see FIG. 5A)) is included in the blood pressure monitoring module 100, the blood pressure monitoring module 100 itself may estimate a blood pressure, and the microprocessor module that is included in the processor 102 that is provided external to the blood pressure monitoring module 100 may perform a control function of transmitting data about the blood pressure estimated by the blood pressure monitoring module 100 to the user interface module 101.

Figure 5A:
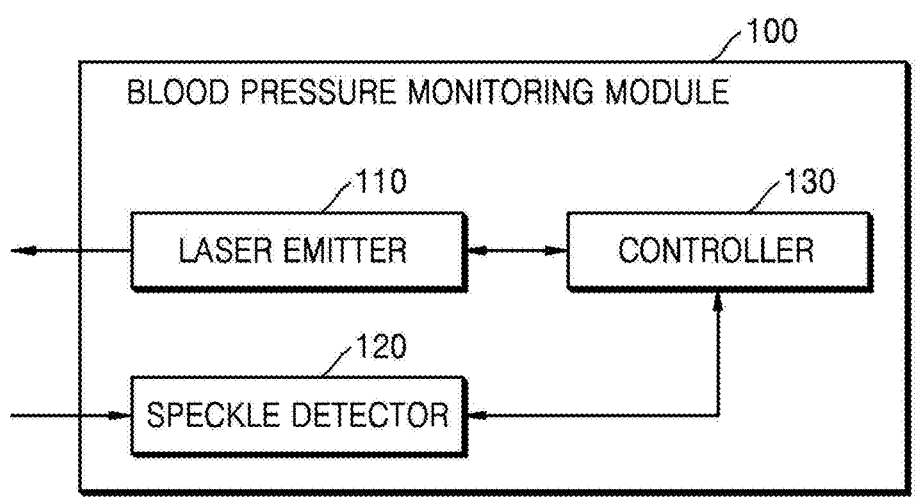
FIG. 5A is a block diagram illustrating a hardware configuration of the blood pressure monitoring module mounted in the wearable device, according to an exemplary embodiment.

FIG. 5A is a block diagram illustrating a hardware configuration of the blood pressure monitoring module 100 that is mounted in the wearable device 10, according to an exemplary embodiment.

Referring to FIG. 5A, the blood pressure monitoring module 100 may include a laser emitter 110, a speckle detector 120, and the controller 130. For clarity, only certain elements of the blood pressure monitoring module 100 are shown in FIG. 5A. Accordingly, it will be understood by one of ordinary skill in the art that the blood pressure monitoring module 100 may further include additional general-purpose elements other than the elements shown in FIG. 5A. Although the controller 130 may be realized as a microprocessor module of the processor 102 described with reference to FIG. 4, the exemplary embodiments are not limited thereto.

Although the blood pressure monitoring module 100 may be embedded in the wearable device 10 at the specific position 300 (see FIG. 3) of the wearable device 10 as described above, the exemplary embodiments are not limited thereto and the blood pressure monitoring module 100 may be embedded at any other position of the wearable device 10.

The laser emitter 110 emits a laser to a blood vessel (for example, a radial artery) in a body part (for example, a wrist). The laser emitter 110 may include at least one laser diode device that oscillates a laser. In addition to the laser diode device, the laser emitter 110 may include a laser diode driver that controls laser oscillation.

The speckle detector 120 detects laser speckles caused by scattering of the reflected laser from the body part (for example, the wrist). The term "laser speckles" refers to the irregular pattern that is produced due to interference or scattering when a coherent laser is reflected from a surface. The laser speckles may be observed as scattered points in an image of the body part to which the laser is emitted.

Figure 5B:
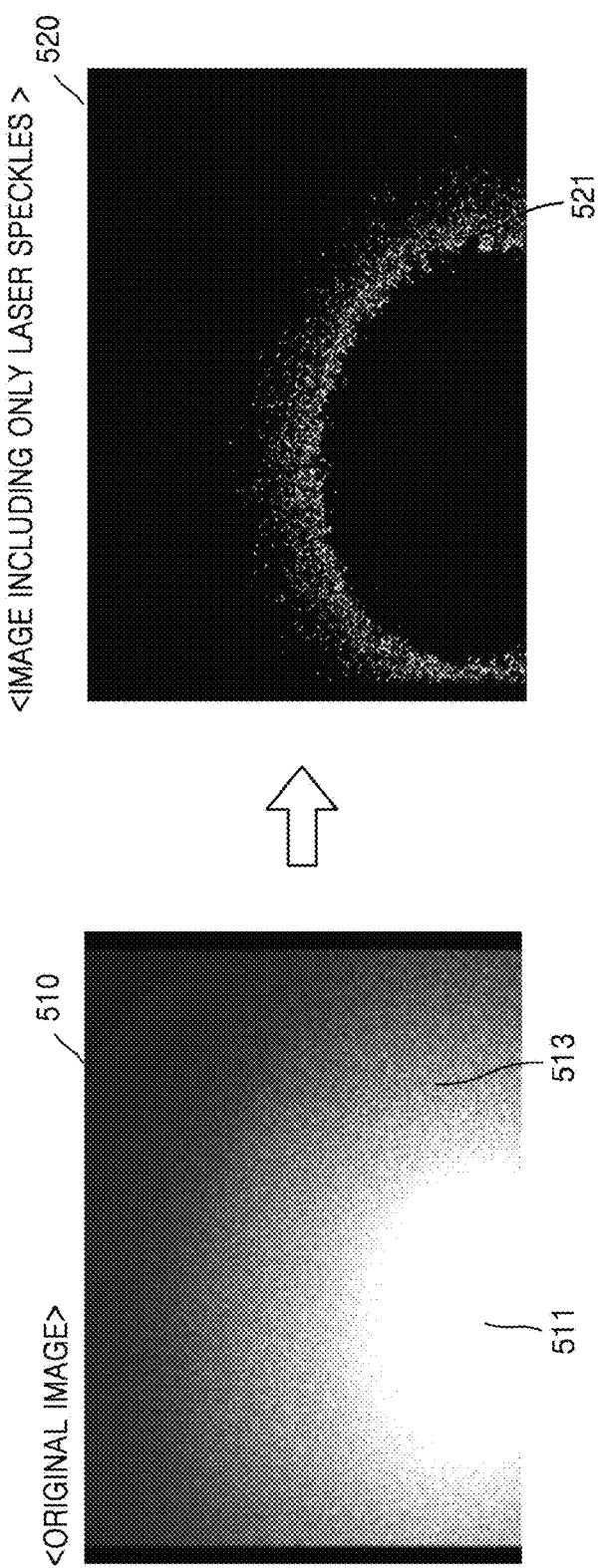
FIG. 5B illustrates images of a body part to which a laser is emitted and a laser speckle, according to an exemplary embodiment.

FIG. 5B illustrates images of a body part to which a laser is emitted and the laser speckles.

Referring to FIG. 5B, an area 511 where a laser having linearity is intensively emitted and a laser speckle area 513 caused by scattering or interference may be separately shown in an original image 510 of the body part to which the laser is emitted. Referring to an image 520 including only laser speckles to more clearly show the laser speckle area 513, the laser speckles may be observed as a pattern of points that are irregularly scattered in the laser speckle area 513 of the image 520.

Referring back to FIG. 5A, the speckle detector 120 may detect an optical signal corresponding to the laser speckles. In detail, the speckle detector 120 may not directly photograph the laser speckles of FIG. 5B, but may detect an optical signal corresponding to the reflection of the laser from the laser speckles and may detect a relationship between an intensity of the optical signal and time. That is, the speckle detector 120 may detect a fluctuation in the intensity of the laser speckles.

The amount of blood flowing in a blood vessel (for example, a radial artery) may change with time as the heart contracts or expands, and thus the volume of the blood vessel may also change with time. Accordingly, when a laser is emitted to the blood vessel, the position of the laser speckle area 513 or 521 (see FIG. 5B) may change as the volume of the blood vessel changes. As such, a phenomenon in which a position of a laser speckles changes may be referred to as a speckle fluctuation.

When the speckle detector 120 continuously receives an optical signal corresponding to the reflection of the laser from the laser speckles, the optical signal may continuously change as the volume of the radial artery changes.

The speckle detector 120 may include at least one photodetecting device. The photodetecting device may include a device, for example, a photodiode device or a phototransistor, which converts the optical signal into an electrical signal. Accordingly, the speckle detector 120 may receive the optical signal corresponding to the laser speckle by using the photodetecting device and may detect a change in the intensity of the optical signal.

The controller 130 obtains a bio-signal indicating the change in the volume of the blood vessel (for example, the radial artery) by using the detected laser speckles, and estimates a blood pressure based on the obtained bio-signal.

The controller 130 may obtain the bio-signal based on the relationship between the intensity of the optical signal that is received by the speckle detector 120 and time. That is, the controller 130 may obtain the bio-signal by analyzing the speckle fluctuation of the laser speckles, which may correspond to the change in the volume of the blood vessel (for example, the radial artery). The obtained bio-signal may be a photoplethysmogram (PPG) signal that is obtained based on a correlation between the analyzed speckle fluctuation and the change in volume. Because the laser speckles detected by the speckle detector 120 are detected as the change in the intensity of the optical signal, and because the change in the intensity of the optical signal is caused by the change in the volume of the blood vessel, the change in the intensity of the optical signal that is detected by the speckle detector 120 may correspond to the PPG signal.

The controller 130 may estimate a systolic blood pressure and a diastolic blood pressure of the user by analyzing waveform characteristics of the PPG signal by using predetermined algorithms for calculating a blood pressure from the PPG signal.

The controller 130 may correspond to a microprocessor module of the processor 102 (see FIG. 4) as described above.

Figure 6:
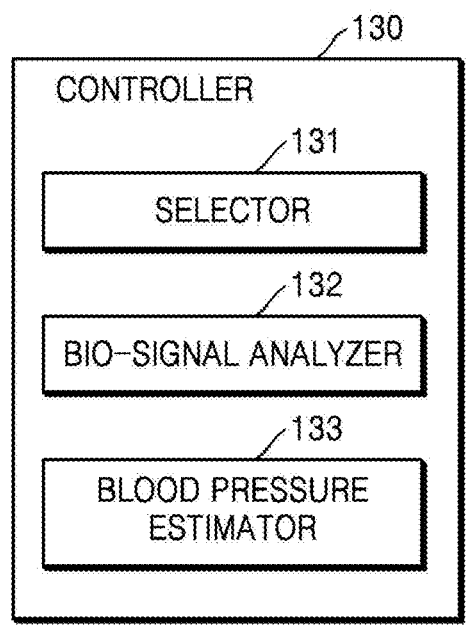
FIG. 6 is a block diagram illustrating a detailed hardware configuration of a controller, according to an exemplary embodiment.

FIG. 6 is a block diagram illustrating a detailed hardware configuration of the controller 130, according to an exemplary embodiment.

Referring to FIG. 6, the controller 130 may include a selector 131, a bio-signal analyzer 132, and a blood pressure estimator 133. For clarity, only certain elements of the controller 130 are shown in FIG. 6. Accordingly, it will be understood by one of ordinary skill in the art that the controller 130 may further include additional general-purpose elements other than the elements shown in FIG. 6, or that some of the elements shown in FIG. 6 may be omitted.

When the speckle detector 120 includes a plurality of photodetecting devices, the selector 131 may select at least one from among the plurality of photodetecting devices based on a detection sensitivity of each of the plurality of photodetecting devices. That is, when the speckle detector 120 includes a plurality of photodetecting devices, the selector 131 may select some photodetecting devices having higher detection sensitivities from among the plurality of photodetecting devices. However, the controller 130 may optionally activate this operation of the selector 131. That is, the controller 130 may deactivate the operation of the selector 131 to select only some photodetecting devices, and thus the controller 130 may set results that are detected by all of the photodetecting devices to be used to estimate a blood pressure.

The bio-signal analyzer 132 converts a change in an intensity of an optical signal corresponding to a speckle fluctuation of the laser speckles detected for a predetermined period of time after a laser is emitted into a PPG signal. When an operation of the selector 131 is activated, the bio-signal analyzer 132 may convert only an optical signal that is detected by a photodetecting device that is selected by the selector 131 into a PPG signal. However, when an operation of the selector 131 is deactivated, the bio-signal analyzer 132 may convert optical signals that are detected by all photodetecting devices into PPG signals.

The blood pressure estimator 133 estimates a systolic blood pressure and a diastolic blood pressure based on waveform characteristics of a PPG signal. When an operation of the selector 131 is activated, the blood pressure estimator 133 may estimate a blood pressure based on the laser speckles detected by a photodetecting device that is selected by the selector 131.

Figure 7:
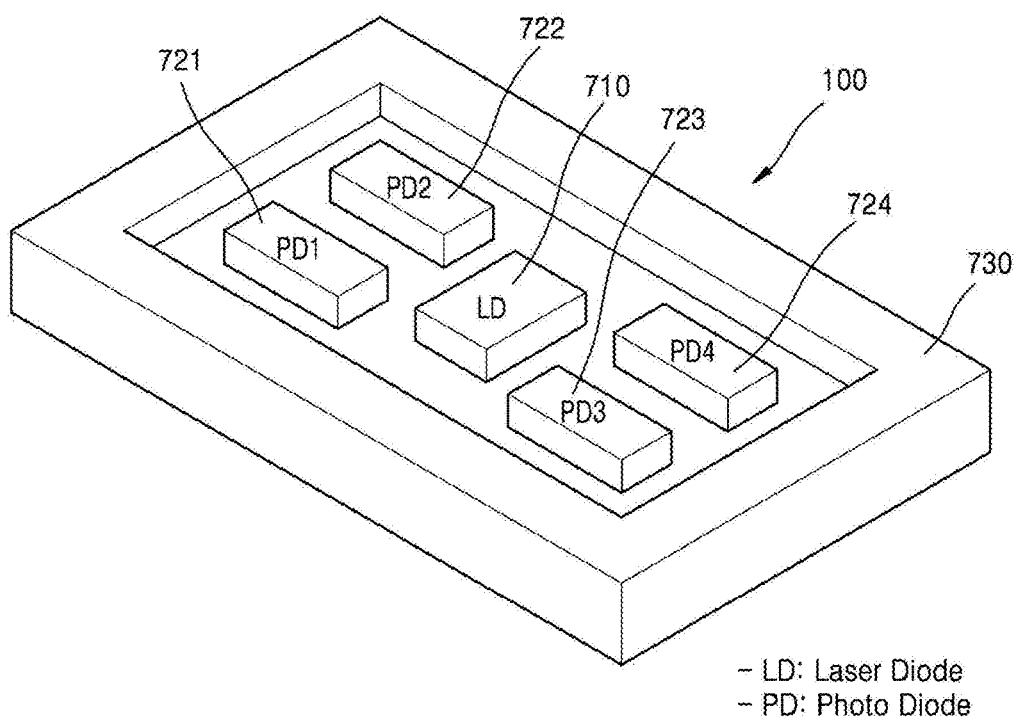
FIG. 7 illustrates a packaging structure of the blood pressure monitoring module including a laser diode device of a laser emitter and a photodiode device of a speckle detector, according to an exemplary embodiment.

FIG. 7 illustrates a packaging structure of the blood pressure monitoring module 100 including a laser diode device of the laser emitter 110 and a photodiode device of the speckle detector 120, according to an exemplary embodiment.

Referring to FIG. 7, the blood pressure monitoring module 100 may include one laser diode LD 710 and four photodiodes PDs 721, 722, 723, and 724. However, the quantity of the laser diodes LD 710 and the quantity of the photodiodes PDs 721, 722, 723, and 724 of FIG. 7 are illustrated as an exemplary embodiment, and thus various modifications may be made with regard to the quantity of devices. Also, in the blood pressure monitoring module 100, other devices configured to oscillate a laser, instead of the laser diode LD 710, may be used, and other devices configured to detect a reflected laser, instead of the photodiodes PDs 721, 722, 723, and 724, may be used.

The laser diode LD 710 and the photodiodes PDs 721, 722, 723, and 724 may be packaged on the same circuit board 730. Although the laser diode LD 710 may be provided at the center and the four photodiodes PDs 721, 722, 723, and 724 may be arranged to surround the laser diode LD 710 as shown in FIG. 7, the exemplary embodiments are not limited thereto.

Each of the photodiodes PDs 721, 722, 723, and 724 may be packaged to be located within a predetermined distance from the laser diode LD 710. For example, the photodiodes PDs 721, 722, 723, and 724 may be packaged to be spaced apart by the same distance from the laser diode LD 710. However, the exemplary embodiments are not limited thereto.

For example, the blood pressure monitoring module 100 having the packaging structure of FIG. 7 may be embedded at the position 300 (see FIG. 3) of the wearable device 10.

Figure 8:
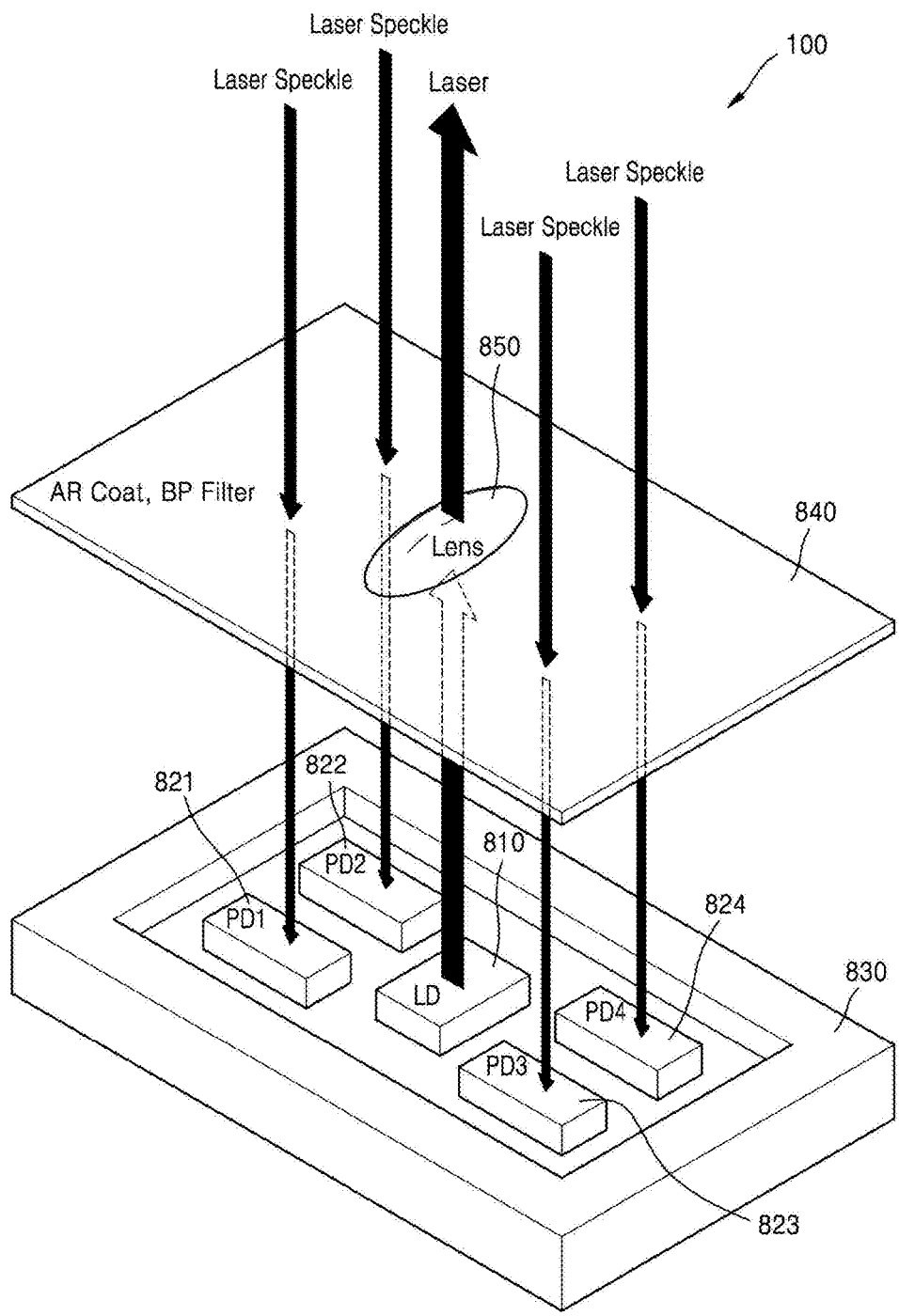
FIG. 8 illustrates a packaging structure of the blood pressure monitoring module in which a transparent substrate is stacked on a circuit board including a laser diode device and a photodiode device, according to an exemplary embodiment.

FIG. 8 illustrates a packaging structure of the blood pressure monitoring module 100 in which a transparent substrate 840 is stacked on a circuit board 830 including a laser diode device and a photodiode device, according to an exemplary embodiment.

Referring to FIG. 8, like in FIG. 7, a laser diode LD 810 and four photodiodes PDs 821, 822, 823, and 824 may be packaged on the circuit board 830. However, in the blood pressure monitoring module 100, other devices configured to oscillate a laser, instead of the laser diode LD 810, may be used and other devices configured to detect a reflected laser, instead of the photodiodes PDs 821, 822, 823, and 824, may be used.

The transparent substrate 840 may be stacked on the circuit board 830. The transparent substrate 840, through which light may pass, may be formed of other materials, such as a glass material, a plastic material, or polydimethylsiloxane (PDMS). A surface of the transparent substrate 840 may be anti-reflection (AR) coated. The transparent substrate 840 is AR coated to prevent the reflection of the laser from the laser speckles from being further reflected. Also, the transparent substrate 840 may be manufactured to perform a bandpass (BP) filter function. The BP filter function of the transparent substrate 840 is to block light other than the reflection of the laser that is reflected from laser speckles. A lens 850 may be inserted into a portion of the transparent substrate 840 through which the laser from the laser diode 810 passes, and a surface of the portion into which the lens 850 is inserted may be free of AR coating. Other lenses, such as a cylindrical lens, a flat lens, a convex lens, a concave lens, a cylindrical convex lens, or a cylindrical concave lens, may be used as the lens 850.

A lens that is separately manufactured may not be able to be inserted into the transparent substrate 840. Therefore, the transparent substrate 840 may be manufactured through injection molding so that a surface of the transparent substrate 840 functions as a lens. However, the exemplary embodiments are not limited thereto, and the lens 850 may be separately manufactured and inserted into the transparent substrate 840 or a portion of the transparent substrate 840 may be manufactured to function as a lens.

Alternatively, a surface of the transparent substrate 840 may be free of AR coating or the transparent substrate 840 may be manufactured without a BP filter function. Surfaces of the photodiodes PDs 821, 822, 823, and 824 may be AR coated or the photodiodes PDs 821, 822, 823, and 824 may be manufactured to perform a BP filter function.

The blood pressure monitoring module 100 having the packaging structure of FIG. 8 may be embedded at position 300 (see FIG. 3) of the wearable device 10.

Figure 9:
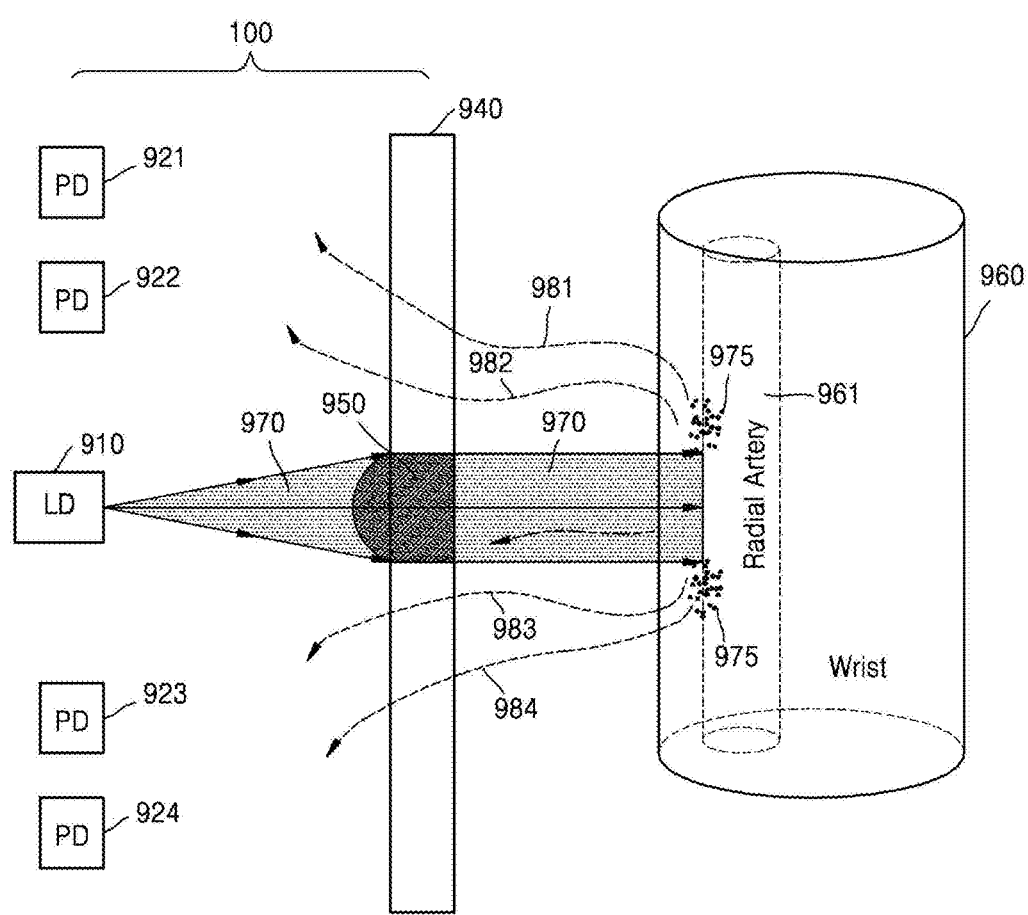
FIG. 9 illustrates a process performed by a laser diode device to emit a laser to a radial artery and a process performed by a photodiode device to detect a reflected laser, according to an exemplary embodiment.

FIG. 9 illustrates a process performed by a laser diode device to emit a laser to a radial artery and a process performed by a photodiode device to detect a reflected laser, according to an exemplary embodiment.

Referring to FIG. 9, a laser diode LD 910 emits a laser 970 to a radial artery 961 in a wrist 960. In this case, the laser 970 may be emitted to the radial artery 961 after passing through a lens 950 that is inserted into a transparent substrate 940.

When the laser 970 is emitted to the radial artery 961, laser speckles 975 may be produced by scattering or interference around a portion of the radial artery 961 on which the laser 970 is incident. Lasers 981, 982, 983, and 984 having the same wavelength band as the laser 970 may be reflected from the laser speckles 975.

The lasers 981, 982, 983, and 984 that are reflected from the laser speckles 975 may pass through the transparent substrate 940 and may be detected by photodiodes PDs 921, 922, 923, and 924.

The lasers 981, 982, 983, and 984 may be detected as optical signals by the photodiodes PDs 921, 922, 923, and 924. An intensity of each of the detected optical signals may change as a volume of the radial artery 961 changes. In detail, when the volume of the radial artery 961 changes, a position of the laser speckles 975 may change. Accordingly, an intensity of each of the optical signals (that is, an intensity of each of the lasers 981, 982, 983, and 984) detected by the photodiodes PDs 921, 922, 923, and 924 may also change.

Laser emission and laser detection of the blood pressure monitoring module 100 of FIG. 9 may be provided using any of the packaging structures of the blood pressure monitoring module 100 of the previous exemplary embodiments.

Figure 10A:
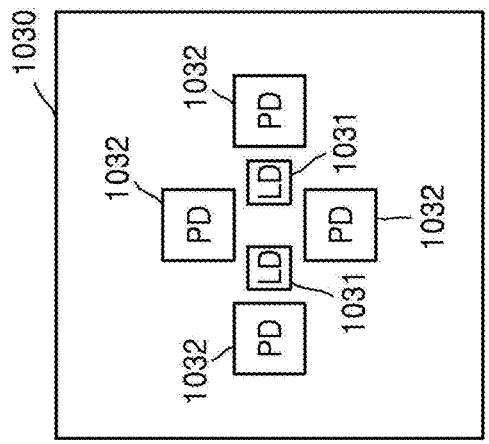
FIGS. 10A, 10B, and 10C are plan views illustrating various packaging structures of laser diode devices and photodiode devices, according to an exemplary embodiment.
Figure 10B:
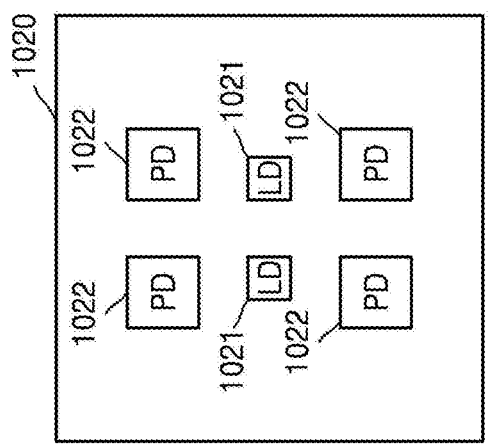
Figure 10C:
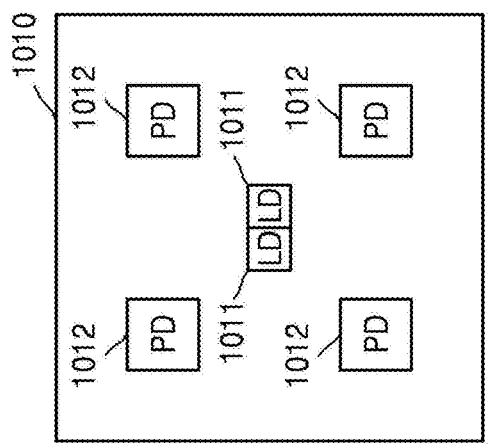

FIGS. 10A through 10C are plan views illustrating various packaging structures of laser diode devices and photodiode devices, according to an exemplary embodiment.

Referring to FIGS. 10A through 10C, although two laser diodes LDs 1011, 1021, or 1031 and four photodiodes PDs 1012, 1022, or 1032 are included in each of the packaging structures, various modifications may be made with respect to the number of each.

As shown in FIGS. 10A, 10B, and 10C, two laser devices LDs 1011, 1021, or 1031 and four photodiodes PDs 1012, 1022, or 1032 may be packaged on the same circuit board 1010, 1020, or 1030. The laser diodes LDs 1011, 1021, or 1031 may be provided at the center of the circuit board 1010, 1020, or 1030 and the photodiodes PDs 1012, 1022, or 1032 may be arranged to surround the laser diodes LDs 1011, 1021, or 1031.

Each of the photodiodes PDs 1012, 1022, or 1032 may be packaged to be located within a predetermined distance from the laser diodes LDs 1011, 1021, or 1031. For example, the photodiodes PDs 1012, 1022, or 1032 may be packaged to be spaced apart by the same distance from the laser diodes LDs 1011, 1021, or 1031. However, the exemplary embodiments are not limited thereto and the photodiodes PDs 1012, 1022, or 1032 may be packaged to be spaced apart by different distances from the laser diodes LDs 1011, 1021, or 1031.

FIGS. 11A-A through 11A-D illustrate various examples of a transparent substrate that may be stacked on a circuit board, according to an exemplary embodiment.

Hereinafter, a lens through which a laser that is emitted from a laser diode LD passes is defined as a first lens and a lens through which a laser that is reflected from the laser speckles passes is defined as a second lens.

Referring to FIG. 11A-A, a cylindrical lens 1111 may be inserted as a first lens and a flat lens 1112 may be inserted as a second lens into a transparent substrate. Referring to FIG. 11A-B, a convex lens 1121 may be inserted as a first lens into a transparent substrate and a second lens may not be provided. That is, the structure of the transparent substrate of FIG. 11A-B may be similar to that of the transparent substrate 840 of FIG. 8. Referring to FIG. 11A-C, a cylindrical lens 1131 may be inserted as a first lens and cylindrical lenses 1132 may be inserted as second lenses into a transparent substrate. Referring to FIG. 11A-D, a convex lens 1141 may be inserted as a first lens and convex lenses 1142 may be inserted as second lenses into a transparent substrate. That is, as shown in FIGS. 11A-A through 11A-D, various types of first lenses and second lenses may be inserted into a transparent substrate. A transparent substrate may also be manufactured to have any combination of FIGS. 11A-A through 11A-D.

FIGS. 11B-A through 11B-D illustrate various examples of a transparent substrate that may be stacked on a circuit board, according to another exemplary embodiment.

Referring to FIGS. 11B-A through 11B-D, unlike in FIGS. 11A-A through 11A-D, a first lens may be a concave lens, a cylindrical concave lens, or a wedge concave lens.

Referring to FIG. 11B-A, a cylindrical concave lens 1115 may be inserted as a first lens and flat lenses 1116 may be inserted as second lenses into a transparent substrate. Referring to FIG. 11B-B, a wedge concave lens 1125 may be inserted as a first lens and flat lenses 1126 may be inserted as second lenses into a transparent substrate. Referring to FIG. 11B-C, a wedge concave lens 1135 may be inserted as a first lens into a transparent substrate and a second lens may not be provided. Referring to FIG. 11B-D, a cross-wedge concave lens 1145 may be inserted as a first lens and a flat lens 1146 may be inserted as a second lens into a transparent substrate. Referring to FIG. 11B-E, a concave lens 1155 may be inserted as a first lens into a transparent substrate and a second lens may not be provided. Referring to FIG. 11B-F, a cross-wedge concave lens 1165 may be inserted as a first lens and convex lenses 1166 may be inserted as second lenses into a transparent substrate. Referring to FIG. 11B-G, a cylindrical concave lens 1175 may be inserted as a first lens and cylindrical convex lenses 1176 may be inserted as second lenses into a transparent substrate. That is, as shown in FIGS. 11B-A through 11B-G, various types of first lenses and second lenses may be inserted into a transparent substrate. A transparent substrate may also be manufactured to have any combination of FIGS. 11B-A through 11B-G.

Figure 12A:
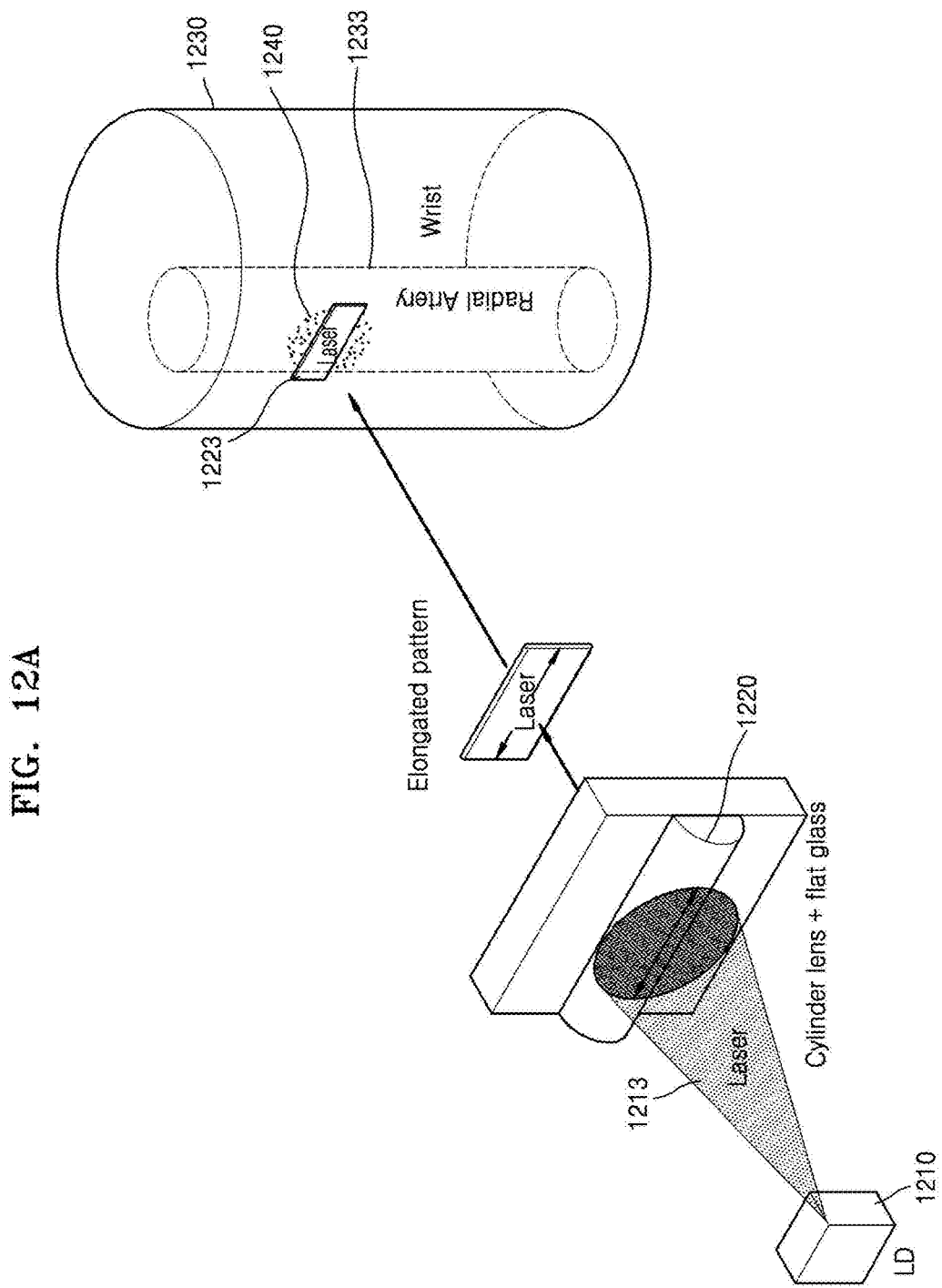
FIG. 12A illustrates a shape of an emitted laser when a cylindrical convex lens is used as a first lens, according to an exemplary embodiment.

FIG. 12A illustrates a shape of an emitted laser when a cylindrical lens is used as a first lens, according to an exemplary embodiment.

Referring to FIG. 12A, when a laser 1213 that is emitted from a laser diode 1210 passes through a cylindrical convex lens 1220 that is inserted into a transparent substrate, a laser 1223 has a narrow elongated pattern. Accordingly, the laser 1223 having the narrow elongated pattern may be emitted towards a radial artery 1233 in a wrist 1230. Accordingly, laser speckles 1240 having a narrow elongated pattern may be produced. That is, a shape of the laser speckles 1240 may vary according to a shape of the laser 1223 that is emitted to the radial artery 1233, and thus an arrangement of photodiodes PDs may change accordingly.

Figure 12B:
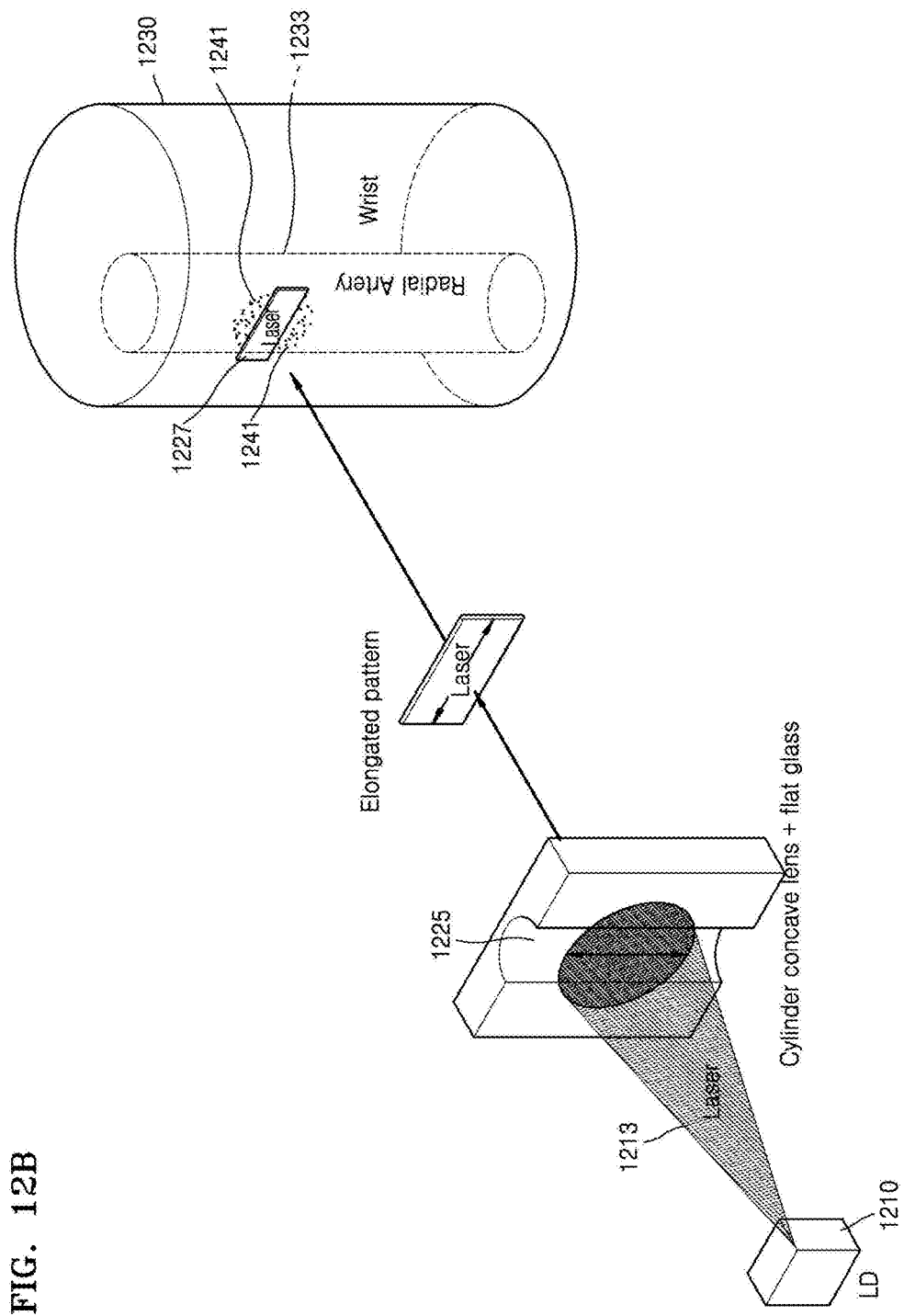
FIG. 12B illustrates a shape of an emitted laser when a cylindrical concave lens is used as a first lens, according to an exemplary embodiment.

FIG. 12B illustrates a shape of an emitted laser when a cylindrical concave lens is used as a first lens, according to another exemplary embodiment.

Referring to FIG. 12B, when a laser 1213 that is emitted from a laser diode 1210 passes through a cylindrical concave lens 1225 that is inserted into a transparent substrate, the laser 1227 has a narrow elongated pattern that is perpendicular to a longitudinal direction of the cylindrical concave lens 1225, unlike in FIG. 12A. Accordingly, the laser 1227 having a narrow elongated pattern may be emitted towards a radial artery 1233 in a wrist 1230. Accordingly, laser speckles 1241 having a narrow elongated pattern may be produced. That is, a shape of the laser speckle 1241 may vary according to a shape of the laser 1227 that is emitted to the radial artery 1233, and thus an arrangement of photodiodes PDs may also change accordingly.

FIGS. 13A through 13D illustrate various emissions of a laser according to a type of a first lens, according to an exemplary embodiment.

Figure 13B:
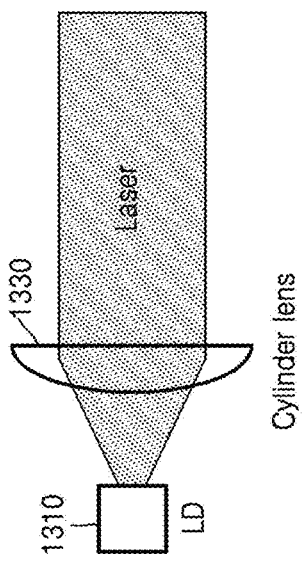
FIGS. 13A, 13B, 13C and 13D illustrate various emissions of a laser according to a type of a first lens, according to an exemplary embodiment.
Figure 13D:
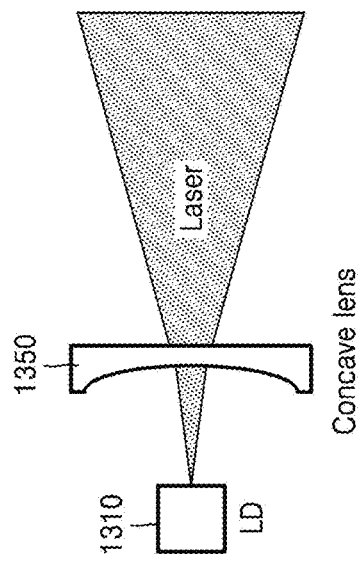
Figure 13A:
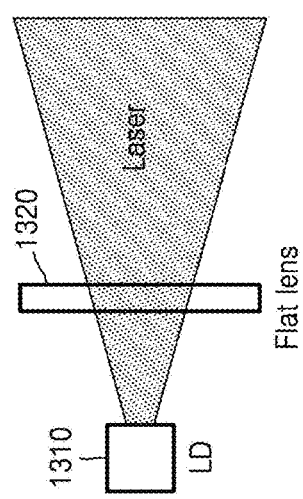
Figure 13C:
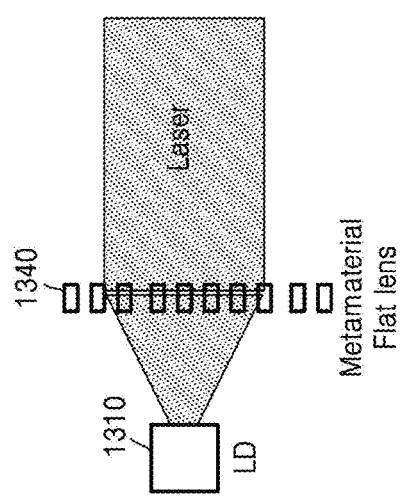

Referring to FIG. 13A, when a laser that is emitted from a laser diode LD 1310 passes through a first lens that is a flat lens 1320, the laser may spread gradually. Referring to FIG. 13B, when a laser that is emitted from the laser diode LD 1310 passes through a first lens that is a cylindrical lens 1330, the laser may be emitted to be concentrated on the center. Even when a first lens is a convex lens, a laser may be emitted to be concentrated on the center, as in the case of the cylindrical lens 1330. Referring to FIG. 13C, when a laser that is emitted from the laser diode LD 1310 passes through a first lens that is a flat lens 1340 formed of a metamaterial, the laser may be emitted to be concentrated on the center. Referring to FIG. 13D, when a laser that is emitted from the laser diode LD 1310 passes through a first lens that is a concave lens 1350, the laser may be emitted to spread gradually.

Although the type of first lens that may be inserted into a transparent substrate may vary according to the position at which the blood pressure monitoring module 100 is embedded in the wearable device 10, the exemplary embodiments are not limited thereto. For example, when the blood pressure monitoring module 100 is close to a radial artery when a user wears the wearable device 10, the first lens may be the flat lens 1320 or the concave lens 1350. However, when the blood pressure monitoring module 100 is far away from the radial artery when the user wears the wearable device 10, if the first lens is the flat lens 1320 or the concave lens 1350, a laser may not be concentrated (or focused) and may spread in all directions, thereby failing to produce laser speckles having a desired range. Accordingly, when the blood pressure monitoring module 100 is far away from the radial artery when the user wears the wearable device 10, the cylindrical lens 1330 may be used as a first lens in order to prevent a laser from spreading irregularly. That is, whether a laser focused by the cylindrical lens 1330 is appropriate or whether a laser that spreads due to the flat lens 1320 or the concave lens 1350 is appropriate may be determined according to the distance between the blood pressure monitoring module 100 and the radial artery when the user wears the wearable device 10. However, even when the distance between the blood pressure monitoring module 100 and the radial artery is fixed, whether a focused laser is appropriate or a spreading laser is appropriate may vary according to various factors, such as the environment in which the wearable device 10 is worn, the type of the laser diode LD 1310, or the type of the photodiode PD. In other words, when the blood pressure monitoring module 100 and the radial artery are spaced apart from each other by a predetermined distance, a focused laser or a spreading laser may not be absolutely useful, and thus the preferred laser may vary according an environment in which the wearable device 10 is worn and an environment in which the wearable device 10 is manufactured.

Figure 14:
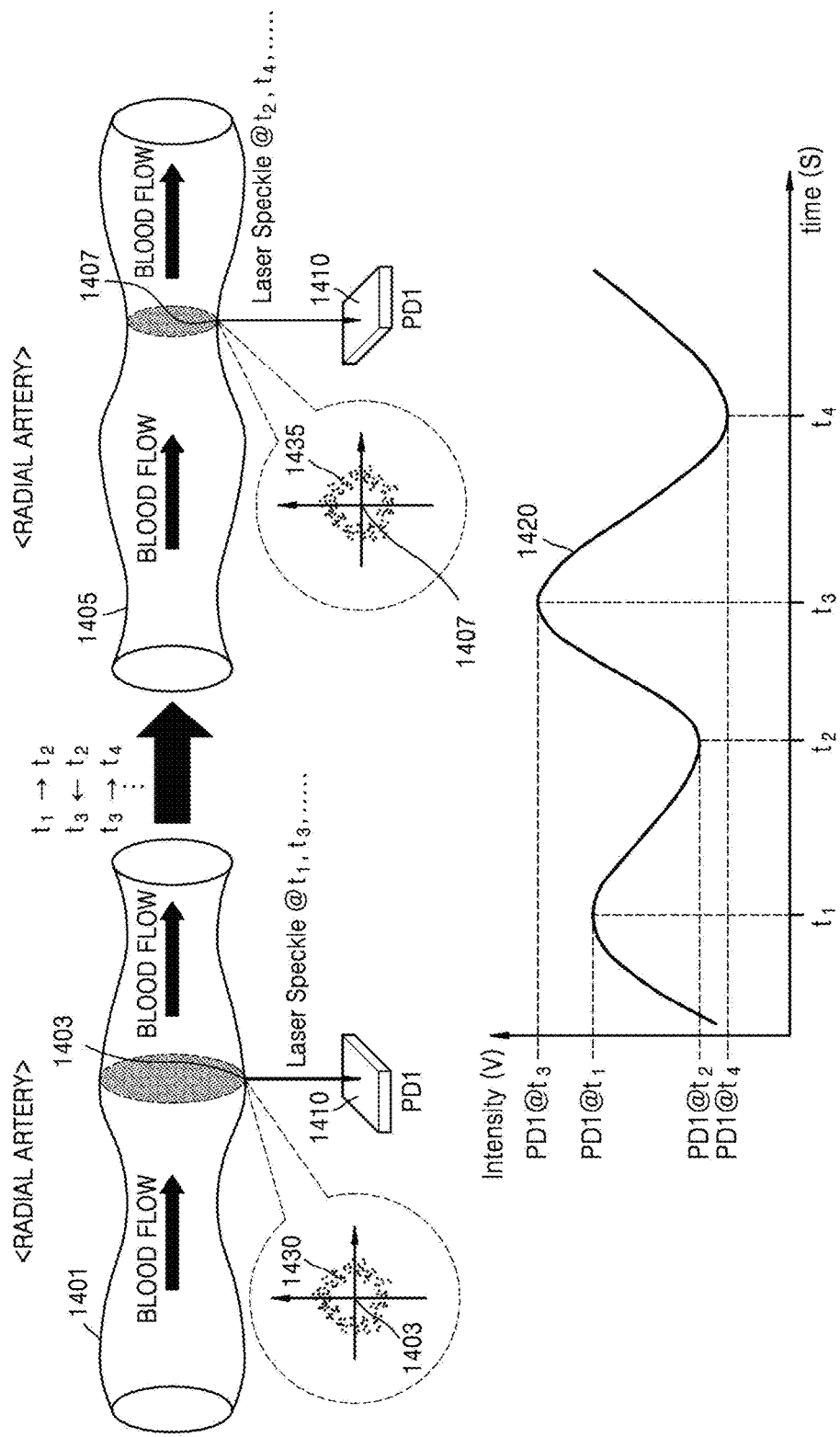
FIG. 14 illustrates a phenomenon in which an intensity of an optical signal that is detected by a photodiode device changes as a volume of a radial artery changes, according to an exemplary embodiment.

FIG. 14 illustrates a phenomenon in which an intensity of an optical signal that is detected by a photodiode device changes as a volume of a radial artery changes, according to an exemplary embodiment.

FIG. 14 shows cross-sectional views illustrating a radial artery state 1401 and a radial artery state 1405 of the same blood vessel in a wrist at different points of time t. For example, the radial artery state 1401 may represent the state of the radial artery at points of time $t_1, t_3, \ldots, t_n$, and the radial artery state 1405 may represent the state of the radial artery at points of time $t_2, t_4, \ldots, t_{n+1}$. A laser of a laser diode LD may be emitted to a point 1403 in the radial artery state 1401, and a laser of the laser diode LD may be emitted to a point 1407 in the radial artery state 1405.

The laser that is emitted to the point 1403 in the radial artery state 1401 at the points of time $t_1, t_3, \ldots, t_n$ may produce laser speckles 1430 circularly distributed about the point 1403. The reflection of the laser from the laser speckles 1430 may be detected by a photodiode PD 1410.

The laser that is emitted to the point 1407 in the radial artery state 1405 at the points of time $t_2, t_4, \ldots, t_{n+1}$ may produce laser speckles 1435 circularly distributed about a point slightly spaced apart rightward from the point 1407. The reflection of the laser from the laser speckles 1435 may be detected by the photodiode PD 1410.

That is, when the amount of blood in the radial artery changes as the heart contracts and expands, because a volume (cross-sectional area) at the point 1403 in the radial artery state 1401 at the points of time $t_1, t_3, \ldots, t_n$ is different from a volume at the point 1407 in the radial artery state 1405 at the points of time $t_2, t_4, \ldots, t_{n+1}$, the position of the laser speckles 1430 may be different from the position of the laser speckles 1435. Accordingly, the intensity of an optical signal (laser) that is detected by the photodiode PD 1410 may be vary over time. That is, a speckle fluctuation may occur.

In detail, a graph 1420 of FIG. 14 shows a relationship between an intensity of an optical signal that is detected by the photodiode PD 1410 and time. For example, when an intensity of an optical signal detected by photodiode PD 1410 at the point of time $t_1$ is "PD1@$t_1$" volts (V), an intensity of an optical signal detected by photodiode PD 1410 at the point of time $t_2$ "PD1@$t_2$" V may be less than the intensity "PD1@$t_1$" V. Also, when an intensity of an optical signal detected by photodiode PD 1410 at the point of time $t_3$ is "PD1@$t_3$" V, an intensity "PD1@$t_4$" V of an optical signal detected by photodiode PD 1410 at the point of time $t_4$ may be less than the intensity "PD1@$t_3$" V. That is, because the intensity of an optical signal detected by the photodiode PD 1410 may vary according to a speckle fluctuation, and the speckle fluctuation is caused by a change in a volume in the radial artery state 1401 or 1405, it may be determined that the change in the volume in the radial artery state 1401 or 1405 is reflected on (mapped to) the change in the intensity of the optical signal that is detected by the photodiode PD 1410. The controller 130 of the blood pressure monitoring module 100 of FIG. 5A, etc. may convert the change in the intensity of the optical signal into a PPG signal.

Although one photodiode PD 1410 provided in FIG. 14, the exemplary embodiments are not limited thereto and an optical signal may be detected by a plurality of photodiodes PDs as provided in the previous embodiments.

Figure 15:
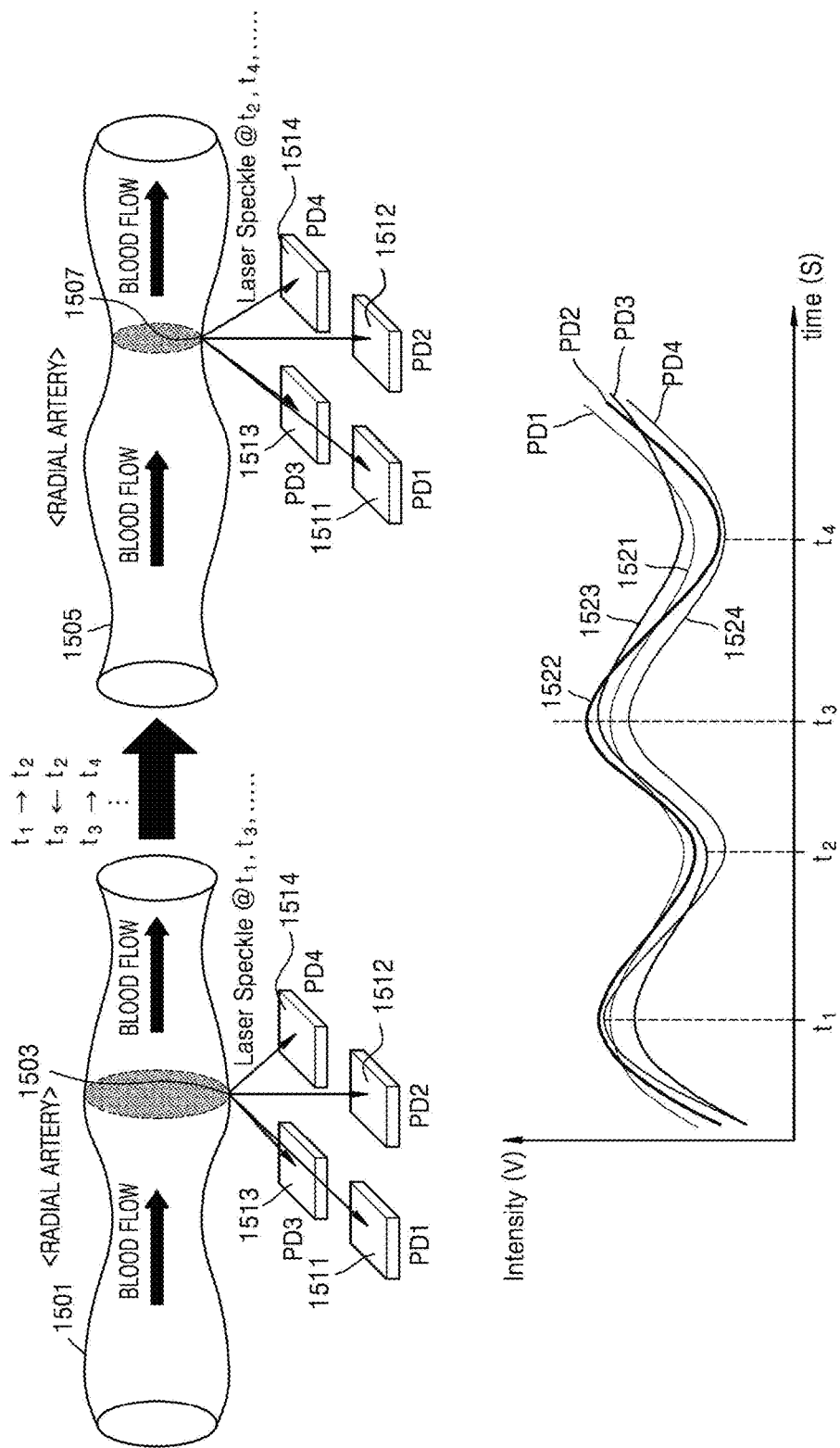
FIG. 15 illustrates optical signals that are detected by a plurality of photodiode devices, according to an exemplary embodiment.

FIG. 15 illustrates optical signals that are detected by a plurality of photodiode devices, according to an exemplary embodiment.

FIG. 15 shows cross-sectional views illustrating a radial artery state 1501 and a radial artery state 1505 of the same blood vessel in a wrist at different points of time. For example, the radial artery state 1501 may represent a state of the radial artery at points of time $t_1, t_3, \ldots, t_n$ and the radial artery state 1505 may represent a state of the radial artery at points of time $t_2, t_4, \ldots, t_{n+1}$. A laser of a laser diode LD may be emitted to a point 1503 in the radial artery state 1501 and a laser of the laser diode LD may be emitted to a point 1507 in the radial artery state 1505.

Unlike in FIG. 14, laser speckles produced by the laser that is emitted to the point 1503 or 1507 may be detected by four photodiodes PDs 1511, 1512, 1513, and 1514.

Referring to graphs 1521, 1522, 1523, and 1524 of FIG. 15, even at the same point of time, intensities of optical signals that are detected by the photodiodes PDs 1511, 1512, 1513, and 1514 may be different from one another. Also, changes in the intensities of the optical signals that are detected by the photodiodes PDs 1511, 1512, 1513, and 1514 may be different from one another. However, as described with reference to FIG. 14, because intensities at the points of time $t_1$ and $t_3$ are greater than intensities at the points of time $t_2$ and $t_4$, the change in the intensities of the optical signals that are detected by the photodiodes PDs 1511, 1512, 1513, and 1514 may be similar to one another. That is, it may be interpreted that a change in a volume in the radial artery state 1501 or 1505 is reflected on (mapped to) the changes in the intensities of the optical signals that are detected by the photodiodes PDs 1511, 1512, 1513, and 1514.

Figure 16:
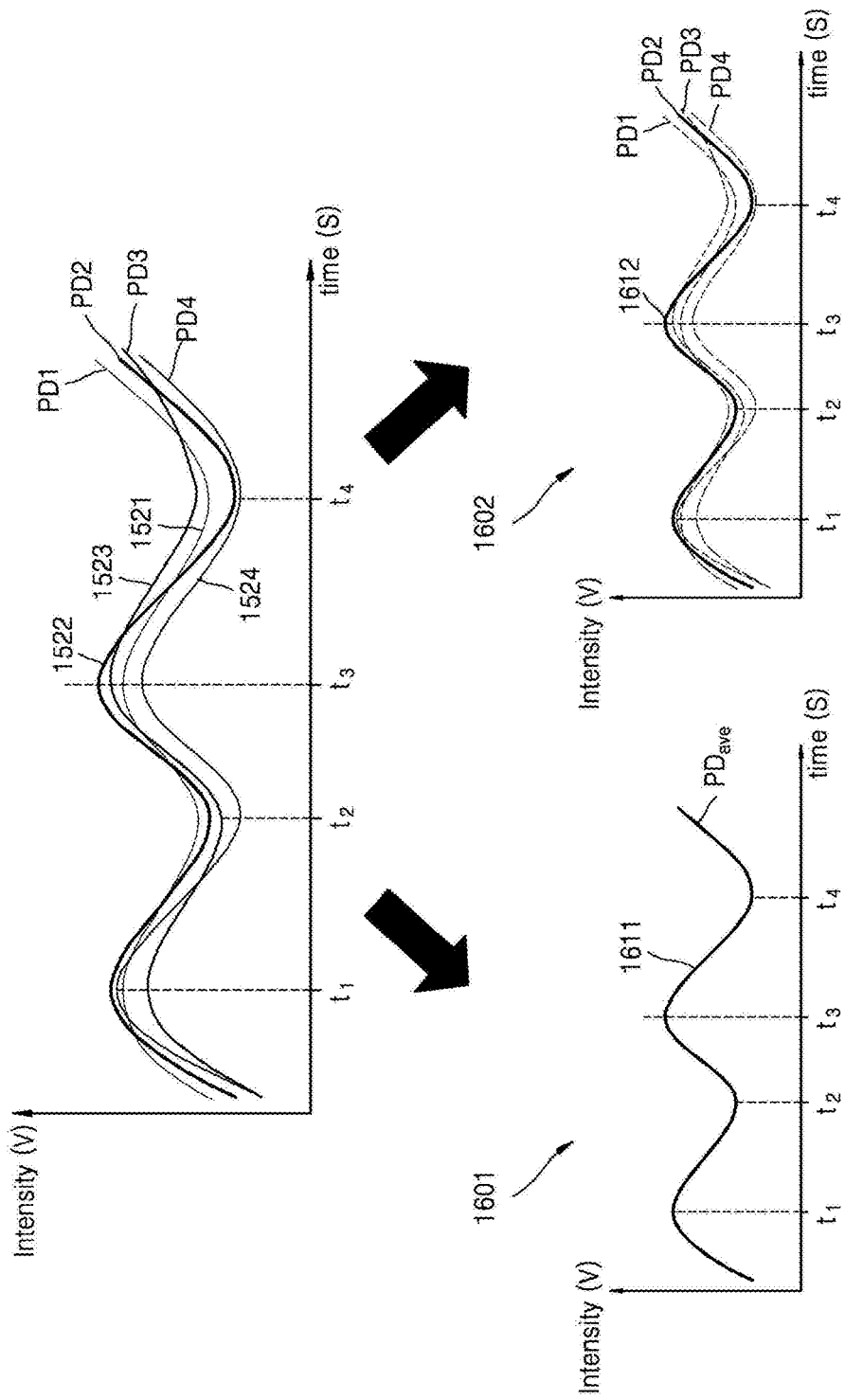
FIG. 16 is a diagram illustrating a process of processing data about a change in intensities of optical signals that are detected by four photodiode devices, according to an exemplary embodiment.

FIG. 16 is a diagram illustrating a process of processing data about changes in intensities of optical signals that are detected by four photodiode devices, according to an exemplary embodiment.

Referring to FIG. 16, graphs 1521, 1522, 1523, and 1524 may correspond to the graphs 1521, 1522, 1523, and 1524 of FIG. 15.

As shown in a diagram 1601 of FIG. 16, the controller 130 of FIG. 5A may obtain one graph 1611 that corresponds to the graphs 1521, 1522, 1523, and 1524 showing changes in intensities of optical signals that are detected by the photodiodes PDs 1511, 1512, 1513, and 1514. The controller 130 may obtain the graph 1611 by calculating an average value of the intensities of the graphs 1521, 1522, 1523, and 1524. Alternatively, the controller 130 may obtain the graph 1611 by using other methods for obtaining a representative value, instead of the average value.

As shown in a diagram 1602 of FIG. 16, the controller 130 may select any one from among the graphs 1521, 1522, 1523, and 1524 showing changes in intensities of optical signals that are detected by the photodiodes PDs 1511, 1512, 1513, and 1514. The selection may be performed by the selector 131 of FIG. 6. The selector 131 may select a graph 1612 corresponding to at least one graph (for example, a graph corresponding to the photodiode PD2 1512) that is determined to have the highest detection sensitivity from among the graphs 1521, 1522, 1523, and 1524.

Furthermore, the controller 130 may process the data of graphs 1521, 1522, 1523, and 1524 by combining methods described with reference to FIG. 16.

Figure 17:
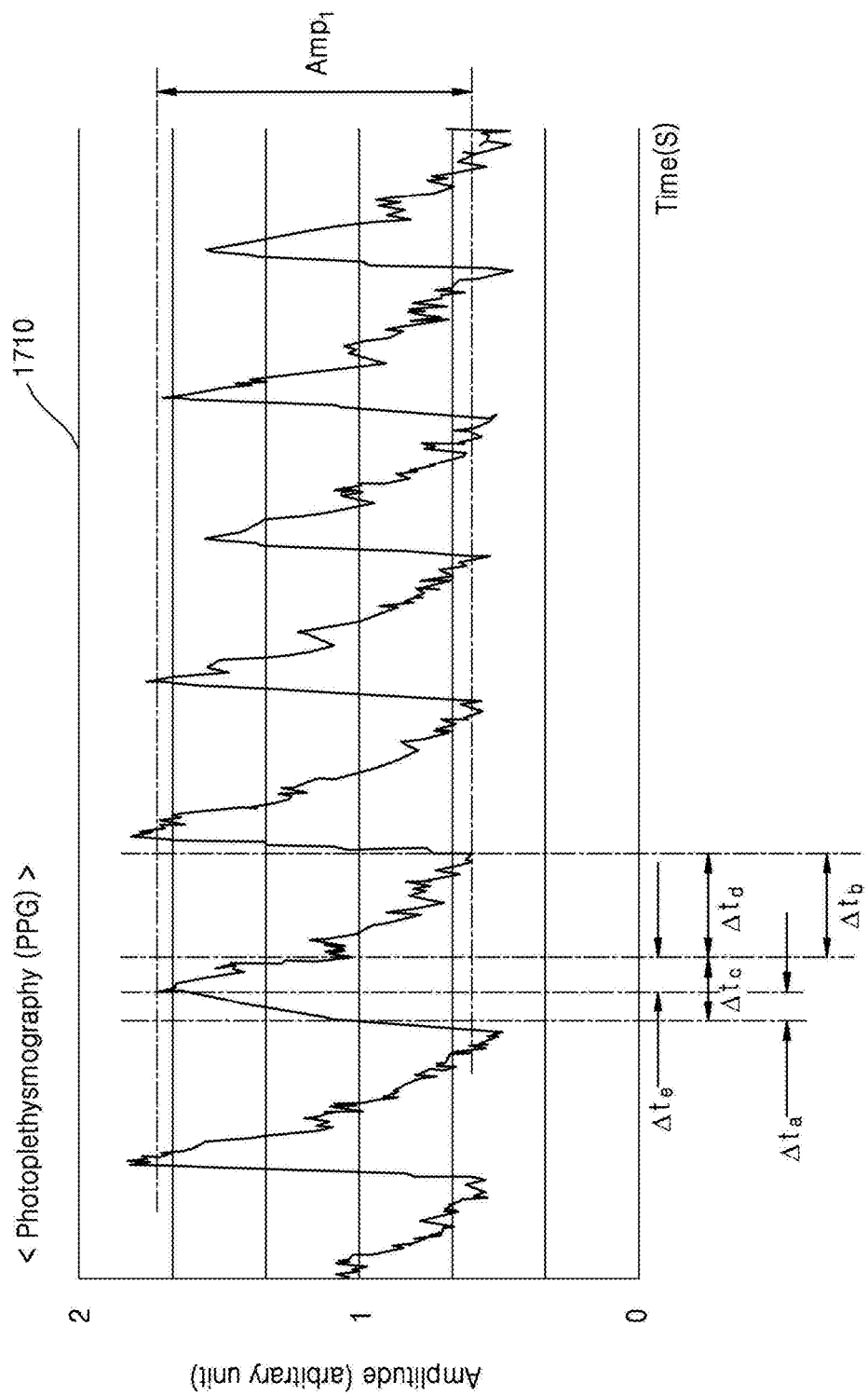
FIG. 17 is a diagram illustrating a bio-signal that is obtained from a change in an intensity of an optical signal that is detected by the speckle detector, according to an exemplary embodiment.

FIG. 17 is a diagram illustrating a bio-signal that is obtained from a change in an intensity of an optical signal that is detected by the speckle detector 120, according to an exemplary embodiment.

Referring to FIG. 17, the bio-signal that is obtained from the change in the intensity of the optical signal that is detected by the speckle detector 120 may be a PPG signal 1710. As described above, the controller 130 may convert the change in the intensity of the optical signal that is detected by the speckle detector 120 into the PPG signal 1710. In detail, the bio-signal analyzer 132 of the controller 130 may obtain the PPG signal 1710 by applying digital signal processing (DSP) algorithms, such as a motion artifact reduction algorithm, a baseline stabilization algorithm, and/or a differential signal extraction algorithm to graph data (for example, data of the graph 1611 or 1612 of FIG. 16) showing the change in the intensity of the optical signal that is detected by the speckle detector 120.

The controller 130, including the blood pressure estimator 133, may estimate a systolic blood pressure and a diastolic blood pressure by using various parameters $\Delta t_a$, $\Delta t_b$, $\Delta t_c$, $\Delta t_d$, and $\Delta t_e$ that are included in the obtained PPG signal 1710. A method of estimating the systolic blood pressure and the diastolic blood pressure from the PPG signal 1710 is well known to one of ordinary skill in the art, and thus a detailed explanation thereof will not be given.

Figure 18:
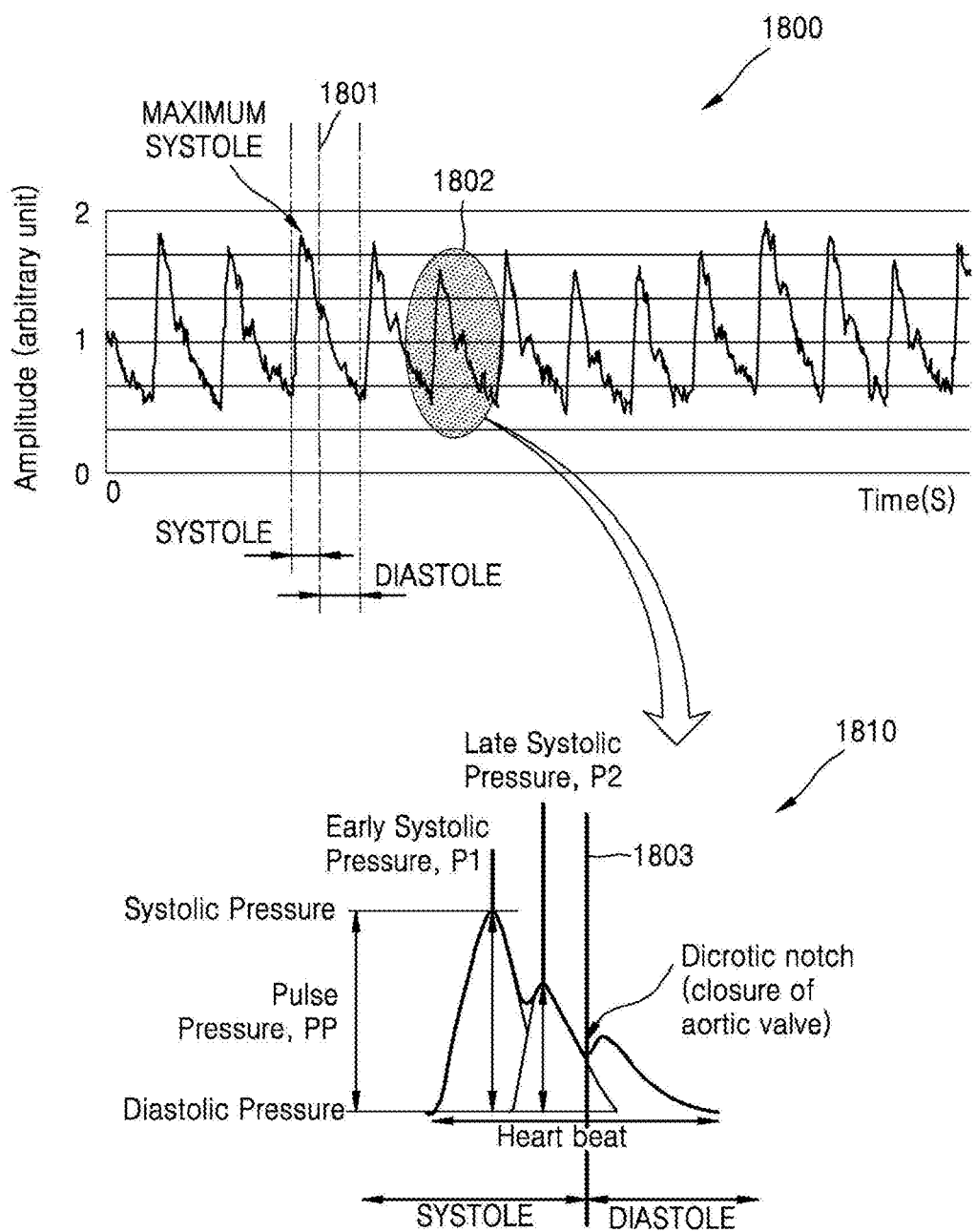
FIG. 18 is a diagram illustrating points of time of a systole and a diastole of the heart shown in a photoplethysmogram (PPG) signal, according to an exemplary embodiment.

FIG. 18 is a diagram illustrating points of time of a systole and a diastole of the heart in a PPG signal, according to an exemplary embodiment.

Referring to a diagram 1800 of FIG. 18, a systole and a diastole of the heart may be divided by a point of time 1801 that is in a waveform of a certain cycle that is included in a PPG signal. Also, a systole and a diastole of the heart may be divided by an inflection point, which is similar to the point of time 1801, in another cycle. Accordingly, the controller 130, including the blood pressure estimator 133, may estimate a systolic blood pressure and a diastolic blood pressure by using information about the parameters $\Delta t_a$, $\Delta t_b$, $\Delta t_c$, $\Delta t_d$, and $\Delta t_e$ of FIG. 17 and information about the points of time 1801 and 1803 of FIG. 18.

A diagram 1810 of FIG. 18 is a detailed graph for explaining bio-information indicated by a waveform 1802 of a certain cycle in the diagram 1800 of FIG. 18. As described above, a systole and a diastole of the heart may be divided by the point 1803 in the waveform 1802. For example, a maximum value of the waveform 1802 may correspond to a systolic blood pressure and a minimum value may correspond to a diastolic blood pressure.

Figure 19:
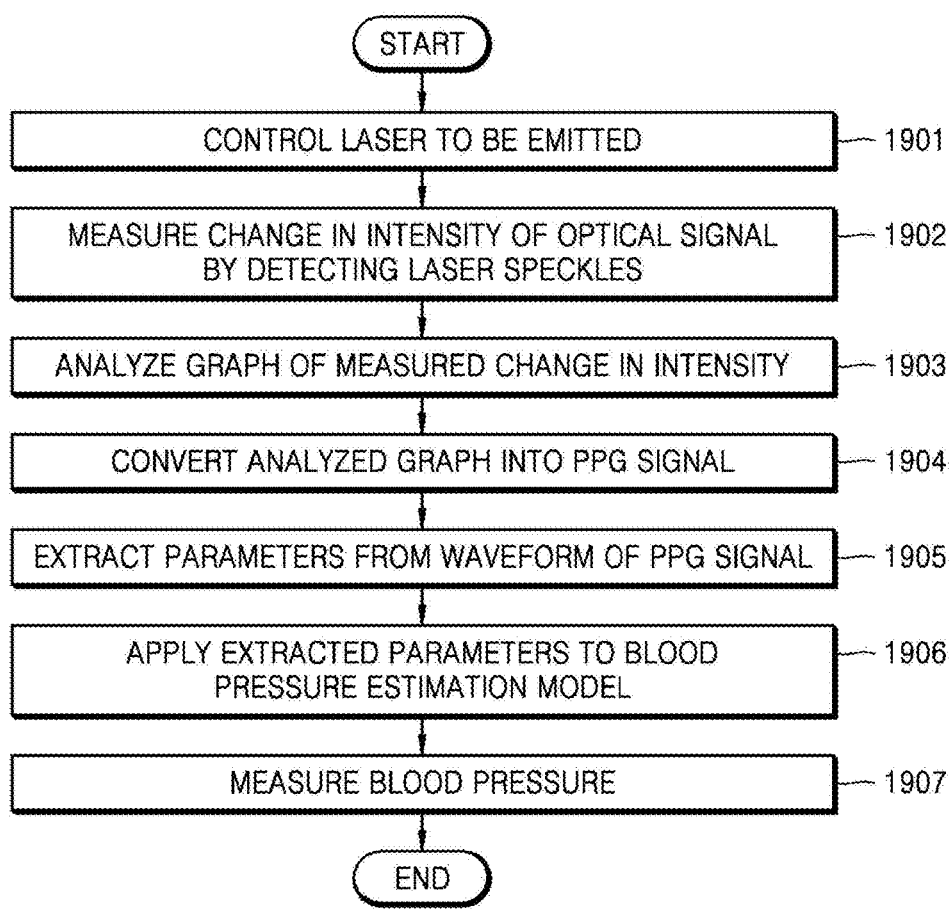
FIG. 19 is a flowchart illustrating a method performed by the blood pressure monitoring module to monitor a blood pressure, according to an exemplary embodiment.

FIG. 19 is a flowchart illustrating a method performed by the blood pressure monitoring module 100 to monitor a blood pressure, according to an exemplary embodiment. Referring to FIG. 19, because the method includes processes that are sequentially processed in the wearable device 10 and the blood pressure monitoring module 100, although omitted herein, the description with regard to the wearable device 10 and the blood pressure monitoring module 100 may also apply to the method of FIG. 19.

In operation 1901, the controller 130 controls oscillation of a laser diode LD of the laser emitter 110 to emit a laser to a radial artery.

In operation 1902, the controller 130 measures a change in an intensity of an optical signal corresponding to laser speckles detected by the speckle detector 120 by controlling the speckle detector 120.

In operation 1903, the controller 130, including the bio-signal analyzer 132, analyzes a graph of the measured change in the intensity by applying DSP algorithms, such as a motion artifact reduction algorithm, a baseline stabilization algorithm, and/or a differential signal extraction algorithm to the graph of the measured change in the intensity.

In operation 1904, the controller 130, including the bio-signal analyzer 132, converts the analyzed graph into a PPG signal based on the results of the analysis.

In operation 1905, the controller 130, including the bio-signal analyzer 132, extracts parameters from a waveform of the PPG signal. For example, the parameters may include information about the parameters $\Delta t_a$, $\Delta t_b$, $\Delta t_c$, $\Delta t_d$, and $\Delta t_e$ of FIG. 17 and the points of time 1801 and 1803 of FIG. 18.

In operation 1906, the controller 130, including the bio-signal analyzer 132, applies the extracted parameters to a blood pressure estimation model. The blood pressure estimation model may be, for example, a linear or non-linear model. Examples of the non-linear model may include a neural network learning model and a model that compares a blood pressure with a blood pressure that is measured by a cuff-type sphygmomanometer.

For example, the controller 130, including the bio-signal analyzer 132, may apply the parameters that are extracted from the waveform of the PPG signal to the neural network learning model. In detail, the term "neural network learning model for blood pressure estimation" is a model that, when specific parameters are input to a query, outputs a final blood pressure that matches the parameters that are input to the query by using a previously learned neural network data set. The term "neural network data set" may correspond to a previously learned database through data mining about a correlation between a blood pressure and parameters in a waveform of a PPG signal. Accordingly, the controller 130, including the bio-signal analyzer 132, may input, for example, the parameters $\Delta t_a$, $\Delta t_b$, $\Delta t_c$, $\Delta t_d$, and $\Delta t_e$ of FIG. 17, to a query of a neural network learning model in order to obtain a final blood pressure from a previously learned neural network data set.

Alternatively, the controller 130, including the bio-signal analyzer 132, may apply the parameters that are extracted from the waveform of the PPG signal to a linear model. For example, a linear model may be "SBP=$a_{SBP}$*T2+$b_{SBP}$, DBP=$a_{DBP}$*T2+$b_{DBP}$". SBP may denote a systolic blood pressure or a maximum blood pressure, DBP may denote a diastolic blood pressure or a minimum blood pressure, $a_{SBP}$ and $b_{SBP}$ may denote constants for calculating a systolic blood pressure, and $a_{DBP}$ and $b_{DBP}$ may denote constants for calculating a diastolic blood pressure. Also, T2 may denote a diastolic time and may correspond to, for example, $\Delta t_b$ of FIG. 17. That is, in order to obtain a final blood pressure, the controller 130, including the bio-signal analyzer 132, may input the parameters that are extracted from the waveform of the PPG signal as a variable of the linear model.

As described above, to estimate a blood pressure, parameters that are extracted from a waveform of a PPG signal are used in a neural network learning model or a linear model. Also, various other linear models or non-linear models for estimating a blood pressure are well known, and thus a detailed explanation thereof will not be given.

In operation 1906, the controller 130, including the blood pressure estimator 133, estimates a systolic blood pressure and a diastolic blood pressure based on a result obtained by applying the extracted parameters to the blood pressure estimation model.

FIG. 20 illustrates a process performed by the wearable device 10 in which the plurality of blood pressure monitoring modules 2001, 2002, and 2003 are embedded to monitor a blood pressure, according to an exemplary embodiment.

Referring to FIG. 20, the plurality of blood pressure monitoring modules 2001, 2002, and 2003 may be embedded in the wearable device 10. Each of the blood pressure monitoring modules 2001, 2002, and 2003 may correspond to the blood pressure monitoring module 100. Accordingly, each of the blood pressure monitoring modules 2001, 2002, and 2003 may independently measure a blood pressure.

As shown in Table 2010 of FIG. 20, the processor 102 (see FIG. 4) of the wearable device 10 may select a blood pressure that is measured by any one blood pressure monitoring module, for example, the blood pressure monitoring module 2002, from among blood pressures that are measured by the blood pressure monitoring modules 2001, 2002, and 2003 as a final blood pressure. Accordingly, the processor 102 may select any one blood pressure monitoring module, for example, the blood pressure monitoring module 2002, based on accuracies of blood pressure measurement of the blood pressure monitoring modules 2001, 2002, and 2003.

As shown in Table 2020 of FIG. 20, the processor 102 of the wearable device 10 may estimate a final blood pressure by calculating a blood pressure that represents the blood pressures that are measured by the blood pressure monitoring modules 2001, 2002, and 2003. In this case, the processor 102 may estimate a final blood pressure by calculating an average value of the blood pressures that are measured by the blood pressure monitoring modules 2001, 2002, and 2003. Alternatively, the processor 102 may estimate a final blood pressure by using various other methods for obtaining a representative value, instead of the average value.

Furthermore, the processor 102 may estimate a final blood pressure by combining methods described with reference to Table 2010 and Table 2020.

Figure 21:
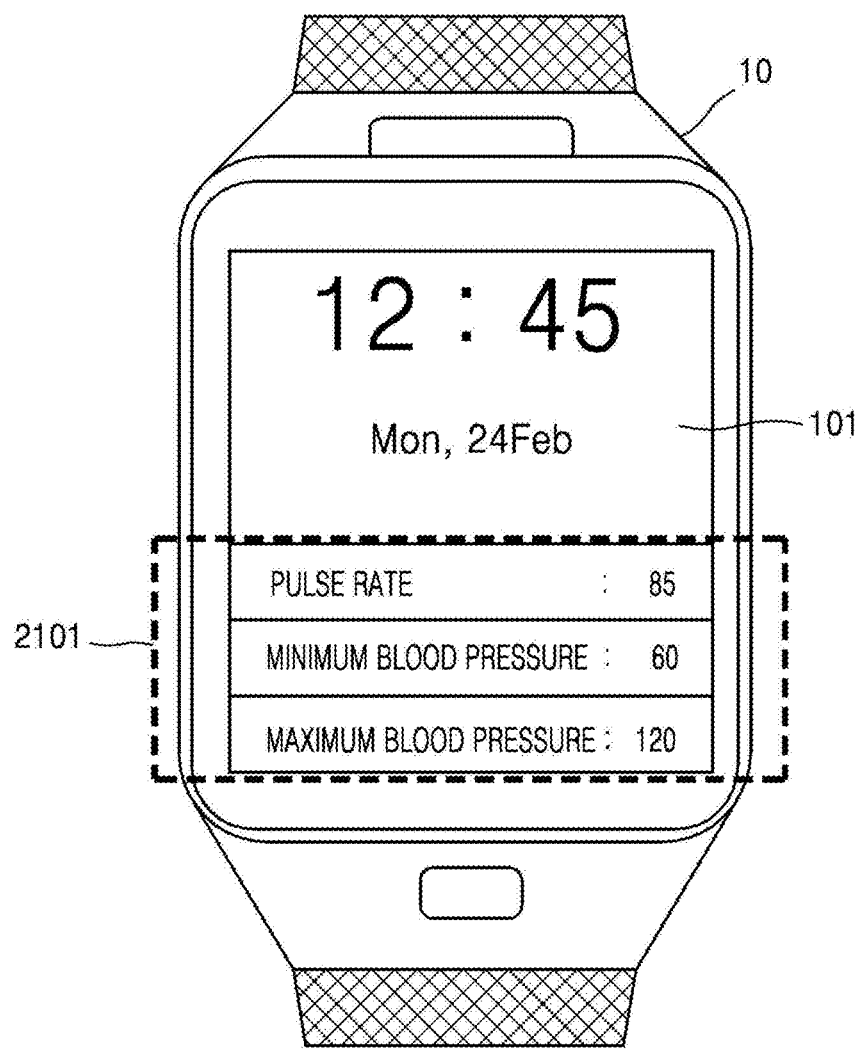
FIG. 21 illustrates a process of providing information about a blood pressure that is monitored by the wearable device, according to an exemplary embodiment.

FIG. 21 illustrates a process of providing information about a blood pressure that is monitored by the wearable device 10, according to an exemplary embodiment.

Referring to FIG. 21, the wearable device 10 may provide blood pressure information 2101 to a user including a pulse rate, a minimum blood pressure, and a maximum blood pressure on a display screen of the user interface module 140.

Figure 22:
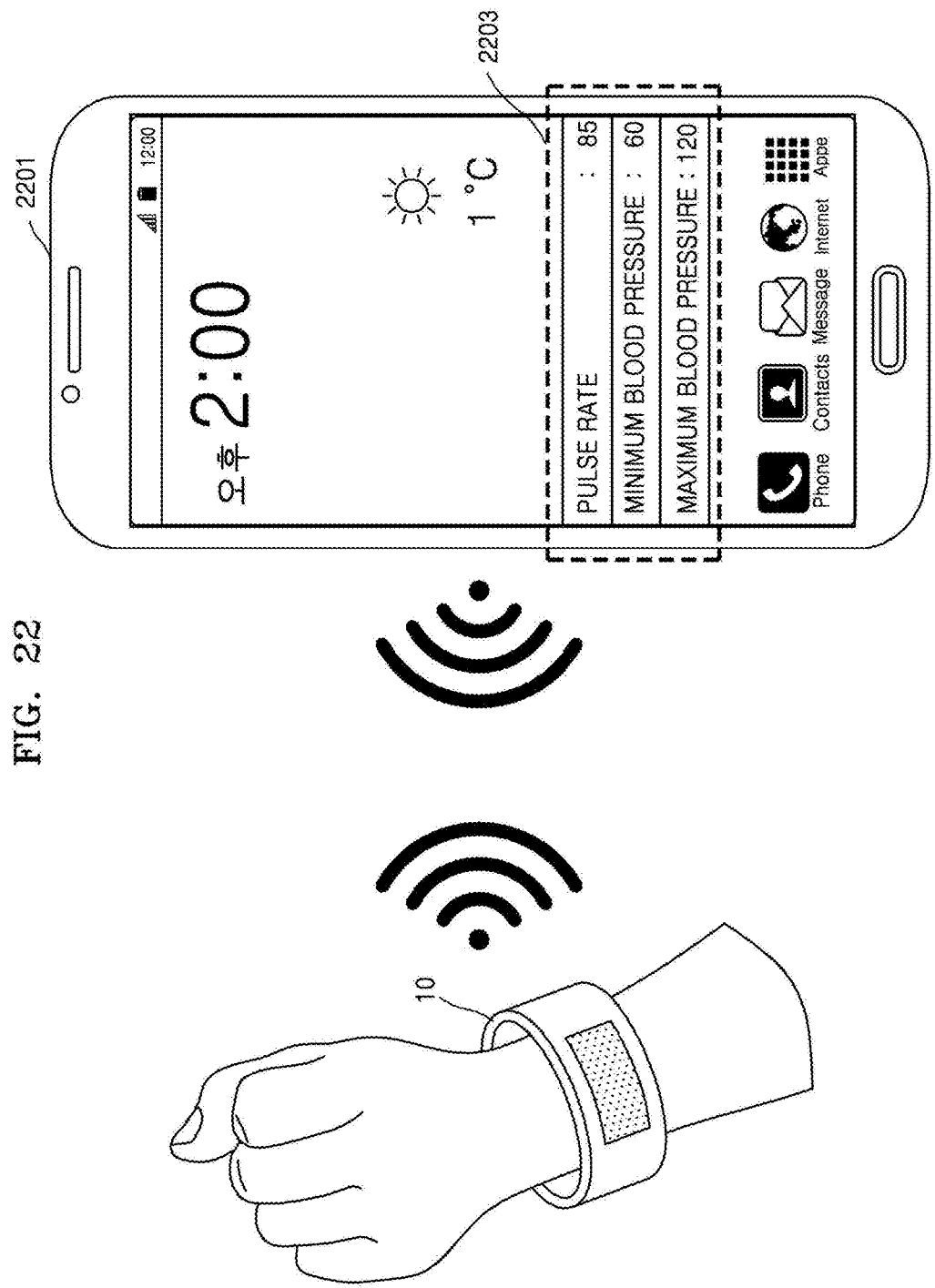
FIG. 22 illustrates a process of providing information about a blood pressure that is monitored by the wearable device, according to an exemplary embodiment.

FIG. 22 illustrates a process of providing information about a blood pressure that is monitored by the wearable device 10, according to another exemplary embodiment.

Referring to FIG. 22, when the wearable device 10 has a wireless communication function such as BLUETOOTH® or WI-FI®, the wearable device 10 may transmit monitored blood pressure information 2203 to a smart phone 2201 of a user by using the wireless communication function. Accordingly, the user may receive the monitored blood pressure information 2203 on a display screen of the smart phone 2201, instead of the wearable device 10.

Figure 23A:
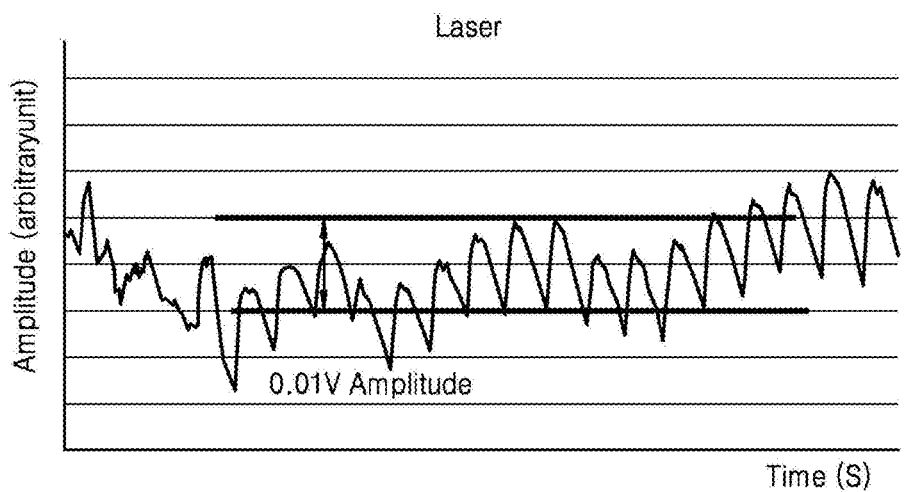
FIGS. 23A and 23B are diagrams illustrating a blood pressure monitoring module using a laser, instead of a light-emitting diode (LED), as a light source, according to an exemplary embodiment.
Figure 23B:
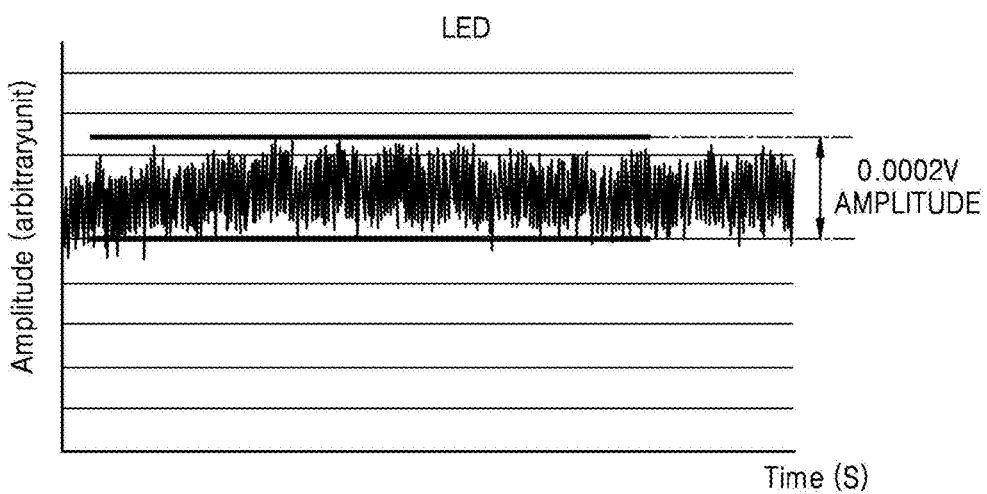

FIGS. 23A and 23B are diagrams illustrating a blood pressure monitoring module 100 using a laser instead of a light-emitting diode (LED) as a light source, according to an exemplary embodiment.

FIG. 23A is a graph showing a result obtained when speckles are detected by using a laser as a light source. FIG. 23B is a graph showing a result obtained when speckles are detected by using an LED as a light source.

Referring to FIG. 23A, an average of waveform amplitudes in cycles of an optical signal corresponding to the speckle that is detected by using the laser may be 0.01 V. Referring to FIG. 23B, an average of waveform amplitudes in cycles of an optical signal corresponding to the speckle that is detected by using the LED may be 0.0002 V. That is, it is found that a speckle detection sensitivity when a speckle is detected by using an LED as a light source is lower than a speckle detection sensitivity when a speckle is detected by using a laser as a light source. This is because the LED has poor linearity compared to the laser. Accordingly, when the blood pressure monitoring module 100 uses an LED as a light source, the accuracy of the blood pressure measurement may be greatly reduced. Accordingly, it is not preferred to replace the laser of the blood pressure monitoring module 100, including the laser emitter 110, with an LED.

Figure 24:
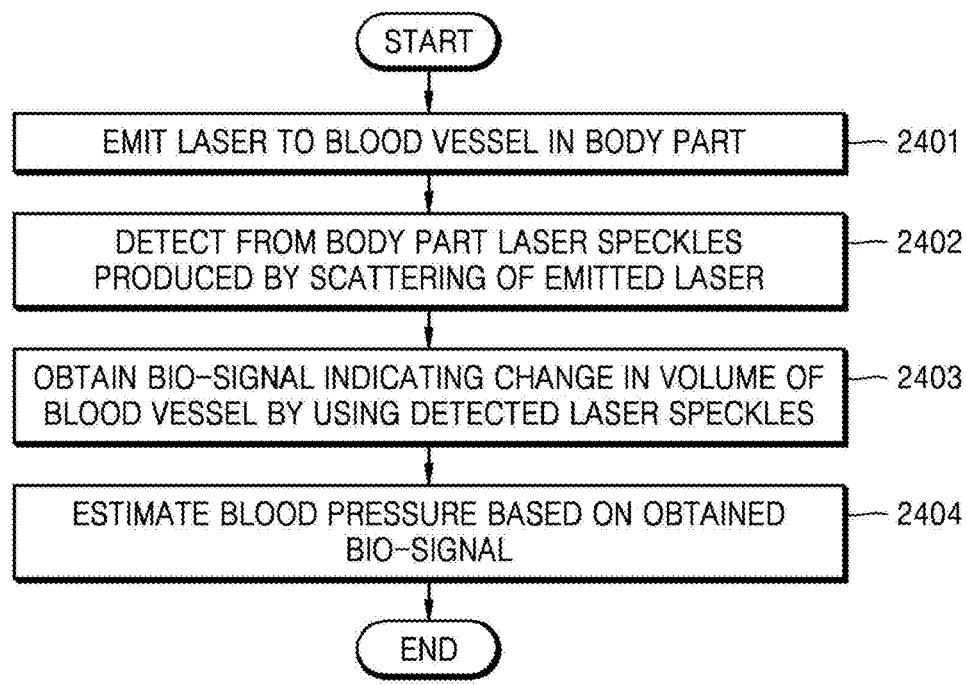
FIG. 24 is a flowchart illustrating a method of monitoring a blood pressure, according to an exemplary embodiment.

FIG. 24 is a flowchart illustrating a method of monitoring a blood pressure, according to an exemplary embodiment. Referring to FIG. 24, because the method includes processes that are sequentially processed in the wearable device 10 and the blood pressure monitoring module 100, although omitted herein, the description with respect to the wearable device 10 and the blood pressure monitoring module 100 may also apply to the method of FIG. 24.

In operation 2401, the laser emitter 110 emits a laser to a blood vessel (for example, a radial artery) in a body part (for example, a wrist).

In operation 2402, the speckle detector 120 detects from the body part laser speckles caused by scattering of the emitted laser.

In operation 2403, the controller 130 obtains a bio-signal indicating a change in a volume of the blood vessel by using the detected laser speckles.

In operation 2404, the controller 130 estimates a blood pressure based on the obtained bio-signal.

As described above, according to one or more of the above exemplary embodiments, because a user's blood pressure may be measured by using a cuffless method, the user's blood pressure may be continuously monitored. Also, because the user's blood pressure may be measured in a non-contact manner or a contact manner by using a sphygmomanometer that is embedded in a wearable device, the user's blood pressure may be conveniently monitored.

The above-described exemplary embodiments may be implemented as an executable program, and may be executed by a general-purpose digital computer that runs the program by using a computer-readable recording medium. Also, the data used in the exemplary method may be recorded by using various units on a computer-readable medium. Examples of the computer-readable medium include storage media such as magnetic storage media (e.g., read only memories (ROMs), floppy discs, or hard discs), optically readable media (e.g., compact disk-read only memories (CD-ROMs), or digital versatile disks (DVDs)), etc.

While the exemplary embodiments have been particularly shown and described with reference to specific terms, the embodiments and terms should not be construed as limiting the scope of the claims. The exemplary embodiments should be considered in a descriptive sense only and not for purposes of limitation. Therefore, the scope of the exemplary embodiments is defined not by the detailed description but by the appended claims, and all differences within the scope will be construed as being included.

What is claimed is:

1. An apparatus for monitoring a blood pressure, the apparatus comprising:
   a laser emitter configured to emit a laser towards a blood vessel in a body part using at least one laser diode device to oscillate the laser;
   a speckle detector configured to detect, from the body part, laser speckles caused by scattering of the laser that is emitted and reflected from the body part; and
   a controller configured to obtain a bio-signal indicating a change in a volume of the blood vessel from the laser speckles and estimate the blood pressure based on the obtained bio-signal,
   wherein the speckle detector comprises a plurality of photodetecting devices,
   wherein the controller is configured to select a photodetecting device having a highest detection sensitivity, from among the plurality of photodetecting devices, and estimate the blood pressure based on the laser speckles detected by the photodetecting device that is selected,
   wherein the detection sensitivity corresponds to a change in an intensity of an optical signal corresponding to a speckle fluctuation of the laser speckles that is received by the speckle detector,
   wherein a number of the photodetecting devices for detecting the laser speckles caused by the at least one laser diode device is more than a number of the at least one laser diode device, and
   wherein each of the plurality of photodetecting devices are packaged around the at least one laser diode device.

2. The apparatus of claim 1, wherein the controller is further configured to obtain the bio-signal by analyzing the speckle fluctuation of the laser speckles detected by at least one photodetecting device, the speckle fluctuation corresponding to the change in the volume of the blood vessel.

3. The apparatus of claim 2, wherein the obtained bio-signal comprises a photoplethysmogram (PPG) signal that is obtained based on the analyzed speckle fluctuation, and
   wherein the detection sensitivity, corresponding to the change in the intensity of the optical signal, corresponds to an average of a waveform amplitude of the PPG signal.

4. The apparatus of claim 1, wherein the controller is further configured to obtain the bio-signal based on a relationship between the intensity of the optical signal corresponding to the speckle fluctuation of the laser speckles that is received by the speckle detector and time.

5. The apparatus of claim 2, wherein the controller is further configured to:
   convert a change in the intensity of the optical signal corresponding to the speckle fluctuation of the laser speckles detected for a predetermined period of time after the laser is emitted into a photoplethysmogram (PPG) signal; and
   estimate a systolic blood pressure and a diastolic blood pressure based on waveform characteristics of the PPG signal.

6. The apparatus of claim 1, wherein the laser emitter comprises at least one laser diode device configured to oscillate the laser,
   wherein the at least one laser diode device and the plurality of photodetecting devices are packaged on a common substrate.

7. The apparatus of claim 6, wherein each of the plurality of photodetecting devices is packaged on the common substrate at a same distance from the at least one laser diode device.

8. The apparatus of claim 7, wherein the plurality of photodetecting devices are symmetrically spaced from the at least one laser diode device.

9. The apparatus of claim 6, further comprising a second substrate stacked on the common substrate, wherein the second substrate includes at least one selected from a first lens through which the emitted laser passes and a second lens through which a laser reflected from the laser speckles passes, and a surface into which the first lens and the second lens are not inserted and which is anti-reflection (AR) coated.

10. The apparatus of claim 9, wherein each of the first lens and the second lens comprises at least one selected from a cylindrical lens and a flat lens.

11. The apparatus of claim 9, wherein the emitted laser and the reflected laser corresponding to the laser speckles are in a same wavelength band.

12. A wearable device configured to monitor a blood pressure, the wearable device comprising:
   at least one blood pressure monitoring module configured to measure a blood pressure of a user;
   a user interface module configured to provide information about the blood pressure; and
   a processor that controls the at least one blood pressuring monitoring module and the user interface module,
   wherein each of the at least one blood pressure monitoring module comprises:
   a laser emitter configured to emit a laser towards a blood vessel in a body part using at least one laser diode device to oscillate the laser;
   a speckle detector configured to detect, from the body part, laser speckles caused by scattering of the laser that is emitted laser and reflected from the body part; and
   a controller configured to obtain a bio-signal indicating a change in a volume of the blood vessel from the laser speckles and estimate the blood pressure based on the obtained bio-signal,
   wherein the speckle detector comprises a plurality of photodetecting devices,
   wherein the controller is configured to select a photodetecting device having a highest detection sensitivity, from among the plurality of photodetecting devices, and estimate the blood pressure based on the laser speckles detected by the photodetecting device that is selected, wherein the detection sensitivity corresponds to a change in an intensity of an optical signal corresponding to a speckle fluctuation of the laser speckles that is received by the speckle detector, wherein a number of the photodetecting devices for detecting the laser speckles caused by the at least one laser diode device is more than a number of the at least one laser diode device, and wherein each of the plurality of photodetecting devices are packaged around the at least one laser diode device.

13. The wearable device of claim 12, wherein the controller is further configured to obtain the bio-signal by analyzing the speckle fluctuation of the laser speckles, the speckle fluctuation corresponding to the change in the volume of the blood vessel, wherein the speckle fluctuation is analyzed based on a relationship between an intensity of an optical signal that is received by the speckle detector and time.

14. The wearable device of claim 12, wherein the wearable device comprises a wristwatch-type device configured to be worn on a wrist of the user, and wherein the blood vessel is a radial artery in the wrist.

15. A method of monitoring a blood pressure, the method comprising:

emitting a laser towards a blood vessel in a body part using at least one laser diode device of a laser emitter to oscillate the laser;

detecting by using a speckle detector, from the body part, laser speckles caused by scattering of the laser emitted and reflected from the body part;

obtaining a bio-signal indicating a change in a volume of the blood vessel from the detected laser speckles; and estimating the blood pressure based on the obtained bio-signal, wherein the speckle detector comprises a plurality of photodetecting devices, wherein the estimating comprises selecting a photodetecting device having a highest detection sensitivity, from among the plurality of photodetecting devices, and estimating the blood pressure based on the laser speckles detected by the photodetecting device that is selected, and wherein the detection sensitivity corresponds to a change in an intensity of an optical signal corresponding to a speckle fluctuation of the laser speckles that is received by the speckle detector, wherein a number of the photodetecting devices for detecting the laser speckles caused by the at least one laser diode device is more than a number of the at least one laser diode device, and wherein each of the plurality of photodetecting devices are packaged around the at least one laser diode device.

16. The method of claim 15, wherein the obtaining the bio-signal is performed by analyzing the speckle fluctuation of the laser speckles, the speckle fluctuation corresponding to the change in the volume of the blood vessel, wherein the speckle fluctuation is analyzed based on a relationship between the intensity of the optical signal that is received by the speckle detector and time.

17. The method of claim 15, wherein the obtaining the bio-signal is performed by converting the change in the intensity of the optical signal corresponding to the speckle fluctuation of the laser speckles detected for a predetermined period of time after the laser is emitted into a photoplethysmogram (PPG) signal, and the estimating the blood pressure comprises estimating a systolic blood pressure and a diastolic blood pressure based on waveform characteristics of the PPG signal.

* * * * *